(12) United States Patent
Kitajima et al.

(10) Patent No.: US 10,948,011 B2
(45) Date of Patent: Mar. 16, 2021

(54) VIBRATION DRIVE DEVICE, IMAGE FORMING APPARATUS, POSITIONING STAGE, AND MEDICAL SYSTEM

(71) Applicant: CANON KABUSHIKI KAISHA, Tokyo (JP)

(72) Inventors: Satoru Kitajima, Kawasaki (JP); Yasumichi Arimitsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1359 days.

(21) Appl. No.: 15/139,425

(22) Filed: Apr. 27, 2016

(65) Prior Publication Data

US 2016/0319860 A1 Nov. 3, 2016

(30) Foreign Application Priority Data

May 1, 2015 (JP) .............................. JP2015-093997

(51) Int. Cl.
*F16C 19/16* (2006.01)
*B25J 17/00* (2006.01)
(Continued)

(52) U.S. Cl.
CPC ............ *F16C 19/166* (2013.01); *A61B 34/30* (2016.02); *B23K 3/087* (2013.01); *B23K 9/028* (2013.01);
(Continued)

(58) Field of Classification Search
CPC .... F16C 19/166; F16C 33/581; F16C 25/083; F16C 2316/10; F16C 2324/16; G03G 2215/00679; G03G 15/6529; G01R 33/28; B23K 11/14; B23K 9/028; B23K 11/16; B23K 26/28; B23K 11/002; B23K 26/32; B23K 2103/05; B23K 3/087; A61B 34/30; B23Q 3/18; B25J 17/00; H02N 2/163
See application file for complete search history.

(56) References Cited

U.S. PATENT DOCUMENTS 6,107,723 A * 8/2000 Fujimoto ............... H02N 2/163
310/323.09
2005/0140357 A1* 6/2005 Takizawa ................ B60T 8/171
324/174

(Continued)

FOREIGN PATENT DOCUMENTS

JP S63-174580 A 7/1988

*Primary Examiner* — Emily P Pham
(74) *Attorney, Agent, or Firm* — Venable LLP

(57) ABSTRACT

A vibration drive device that suppresses an increase in the number of component parts and can be easily downsized. Vibration is excited in a vibration element in pressure contact with a driven element to thereby rotationally move the driven element relative to the vibration element. A bearing rotatably supports the driven element. A first and a second bearing portions are joined to the driven element. The second and a third bearing portions are pressed against each other via rolling elements in a direction along the axis of the bearing. The rolling elements are brought into pressure contact with the first raceway surface of the first bearing portion, the second raceway surface of the second bearing portion, and the third raceway surface of the third bearing portion. One of the second and third bearing portions is integrally formed with the driven element from the same material.

13 Claims, 16 Drawing Sheets

(51) Int. Cl.
| | | |
|---|---|---|
| *B23K 3/08* | (2006.01) | |
| *G03G 15/00* | (2006.01) | |
| *A61B 34/30* | (2016.01) | |
| *B23Q 3/18* | (2006.01) | |
| *B23K 11/14* | (2006.01) | |
| *B23K 9/028* | (2006.01) | |
| *B23K 11/16* | (2006.01) | |
| *B23K 26/28* | (2014.01) | |
| *B23K 11/00* | (2006.01) | |
| *F16C 33/58* | (2006.01) | |
| *B23K 26/32* | (2014.01) | |
| *H02N 2/16* | (2006.01) | |
| *G01R 33/28* | (2006.01) | |
| *F16C 25/08* | (2006.01) | |
| *B23K 103/04* | (2006.01) | |

(52) U.S. Cl.
CPC ............ *B23K 11/002* (2013.01); *B23K 11/14* (2013.01); *B23K 11/16* (2013.01); *B23K 26/28* (2013.01); *B23K 26/32* (2013.01); *B23Q 3/18* (2013.01); *B25J 17/00* (2013.01); *F16C 33/581* (2013.01); *G03G 15/6529* (2013.01); *H02N 2/163* (2013.01); *B23K 2103/05* (2018.08); *F16C 25/083* (2013.01); *F16C 2316/10* (2013.01); *F16C 2324/16* (2013.01); *G01R 33/28* (2013.01); *G03G 2215/00679* (2013.01)

(56) References Cited

U.S. PATENT DOCUMENTS

| | | | | |
|---|---|---|---|---|
| 2011/0255815 | A1* | 10/2011 | Frank | F16C 33/586 384/462 |
| 2014/0343421 | A1* | 11/2014 | Kim | A61B 8/4411 600/438 |

\* cited by examiner

VIBRATION DRIVE DEVICE, IMAGE FORMING APPARATUS, POSITIONING STAGE, AND MEDICAL SYSTEM

BACKGROUND OF THE INVENTION

Field of the Invention

The present invention relates to a vibration drive device which can be easily downsized and in which a vibration element and a driven element are brought into pressure contact with each other, and vibration is excited in the vibration element, to thereby rotationally move the driven element and the vibration element relative to each other, as well as an image forming apparatus, a positioning stage, and a medical system, which use the vibration drive device.

Description of the Related Art

There have been known various vibration drive devices in which a vibration element is formed by joining an electro-mechanical energy conversion element to an elastic body, and predetermined vibration is excited in the vibration element in a state in pressure contact with a driven element, to thereby rotationally move the vibration element and the driven element relative to each other. For example, as a vibration drive device that rotationally moves an annular vibration element and an annular driven element relative to each other, there has been proposed by the present applicant (see e.g. Japanese Patent Laid-Open Publication No. S63-174580) one which is equipped with a bearing which rotatably supports the driven element.

The vibration drive device described in Japanese Patent Laid-Open Publication No. S63-174580 is configured such that an outer ring of the bearing is divided in a thrust direction, and the divided outer rings press rolling elements against each other in a state supported by an inner periphery of an outer hollow cylindrical case (e.g. by threaded engagement, although not specifically described). By thus increasing the stiffness of the bearing, it is possible to obtain stable rotation performance free from wobbling.

However, in the vibration drive device described in Japanese Patent Laid-Open Publication No. S63-174580, to realize the configuration in which the two outer rings formed by dividing the outer ring of the bearing axially press the rolling elements against each other, it is necessary to provide the outer hollow cylindrical case. This brings about problems that the number of component parts is increased and that it is difficult to reduce the size of the vibration drive device.

SUMMARY OF THE INVENTION

The invention provides a vibration drive device that suppresses an increase in the number of component parts and can be easily downsized.

In a first aspect of the present invention, there is provided a vibration drive device in which a vibration element and a driven element are brought into pressure contact with each other, and vibration is excited in the vibration element to thereby rotationally move the driven element relative to the vibration element, the vibration drive device including a bearing rotatably supporting the driven element, the bearing comprising a plurality of rolling elements, a first bearing portion that has a first raceway surface in contact with the rolling elements, a second bearing portion that has a second raceway surface in contact with the rolling elements, and a third bearing portion that has a third raceway surface in contact with the rolling elements, wherein the second bearing portion and the third bearing portion are joined to the driven element, and the second bearing portion and the third bearing portion are pressed against each other in a direction along an axis of the bearing, whereby the rolling elements are brought into pressure contact with the first raceway surface, the second raceway surface, and the third raceway surface and wherein one of the second bearing portion and the third bearing portion is integrally formed with the driven element from a same material.

In a second aspect of the present invention, there is provided a medical system including a multi-joint robot that performs a predetermined diagnosis or operation on a subject, wherein the multi-joint robot has a plurality of joint portions, and each of the joint portions incorporates a vibration drive device in which a vibration element and a driven element are brought into pressure contact with each other, and vibration is excited in the vibration element to thereby rotationally move the driven element relative to the vibration element, in order to enable each joint portion to perform rotational movement, the vibration drive device including a bearing rotatably supporting the driven element, the bearing comprising a plurality of rolling elements, a first bearing portion that has a first raceway surface in contact with the rolling elements, a second bearing portion that has a second raceway surface in contact with the rolling elements, and a third bearing portion that has a third raceway surface in contact with the rolling elements, wherein the second bearing portion and the third bearing portion are joined to the driven element, and the second bearing portion and the third bearing portion are pressed against each other in a direction along an axis of the bearing, whereby the rolling elements are brought into pressure contact with the first raceway surface, the second raceway surface, and the third raceway surface and wherein one of the second bearing portion and the third bearing portion is integrally formed with the driven element from a same material.

In a third aspect of the present invention, there is provided an image forming apparatus including an image forming unit configured to form an image on a sheet using toner or ink; and a conveying unit configured to convey a sheet to the image forming unit or convey a sheet having a predetermined image formed thereon by the image forming unit, wherein the conveying unit is equipped with a vibration drive device which is connected to a roller driven for rotation for conveying a sheet and in which a vibration element and a driven element are brought into pressure contact with each other, and vibration is excited in the vibration element to thereby rotationally move the driven element relative to the vibration element, the vibration drive device including a bearing rotatably supporting the driven element, the bearing comprising a plurality of rolling elements, a first bearing portion that has a first raceway surface in contact with the rolling elements, a second bearing portion that has a second raceway surface in contact with the rolling elements, and a third bearing portion that has a third raceway surface in contact with the rolling elements, wherein the second bearing portion and the third bearing portion are joined to the driven element, and are pressed against each other in a direction along an axis of the bearing, whereby the rolling elements are brought into pressure contact with the first raceway surface, the second raceway surface, and the third raceway surface and wherein one of the second bearing portion and the third bearing portion is integrally formed with the driven element from a same material.

In a fourth aspect of the present invention, there is provided a positioning stage including a vibration drive device in which a vibration element and a driven element are brought into pressure contact with each other, and vibration is excited in the vibration element to thereby rotationally move the driven element relative to the vibration element, and a stage that is moved in a predetermined direction by the vibration drive device, the vibration drive device including a bearing rotatably supporting the driven element, the bearing comprising a plurality of rolling elements, a first bearing portion that has a first raceway surface in contact with the rolling elements, a second bearing portion that has a second raceway surface in contact with the rolling elements, and a third bearing portion that has a third raceway surface in contact with the rolling elements, wherein the second bearing portion and the third bearing portion are joined to the driven element, and are pressed against each other in a direction along an axis of the bearing, whereby the rolling elements are brought into pressure contact with the first raceway surface, the second raceway surface, and the third raceway surface and wherein one of the second bearing portion and the third bearing portion is integrally formed with the driven element from a same material.

According to the present invention, the bearing including the first bearing portion, the second bearing portion, and the third bearing portion is configured such that the second bearing portion and the third bearing portion are joined to the driven element, and the second bearing portion and the third bearing portion are pressed against each other in the direction along the axis of the bearing. With this configuration, the rolling elements are brought into pressure contact with the first raceway surface of the first bearing portion, the second raceway surface of the second bearing portion, and the third raceway surface of the third bearing portion. This makes it possible to suppress an increase in the number of the component parts, and makes it easy to downsize the vibration drive device. Further, it is possible to maintain stable rotation for a long time period.

Further features of the present invention will become apparent from the following description of exemplary embodiments (with reference to the attached drawings).

DESCRIPTION OF THE EMBODIMENTS

The present invention will now be described in detail below with reference to the accompanying drawings showing embodiments thereof.

Figure 1A:
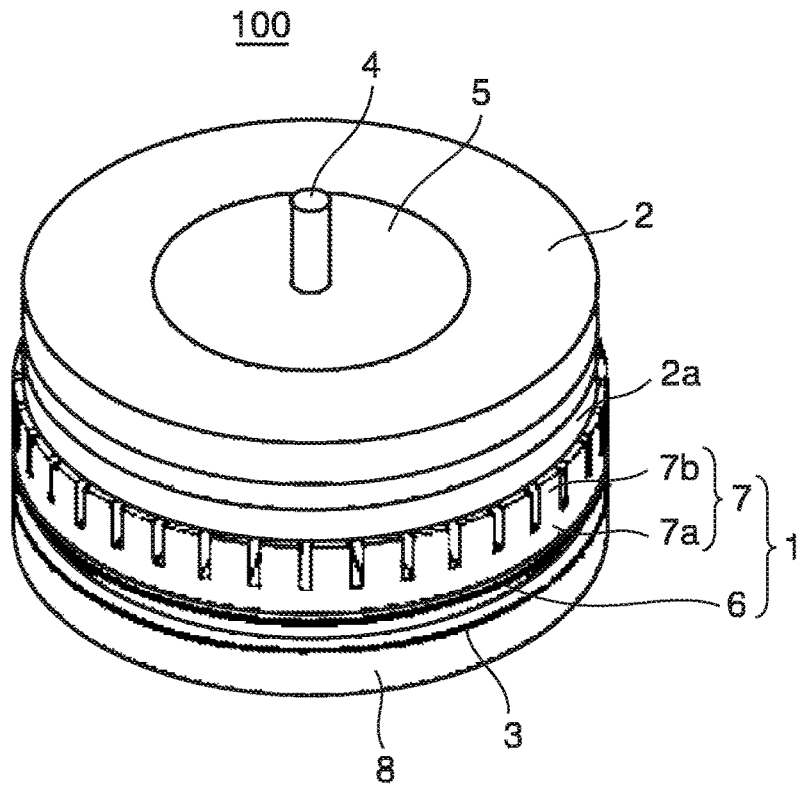
FIG. 1A is a perspective view of a vibration drive device according to a first embodiment of the present invention.
Figure 1B:
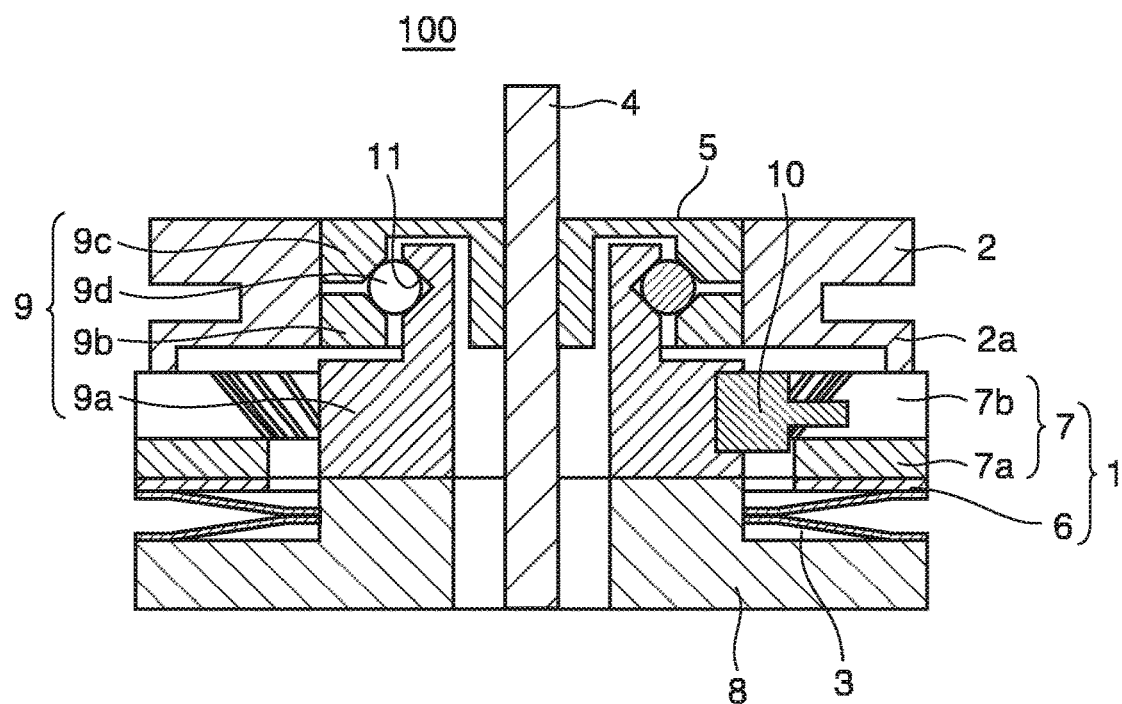
FIG. 1B is a cross-sectional view of the vibration drive device shown in FIG. 1A.
Figure 2:
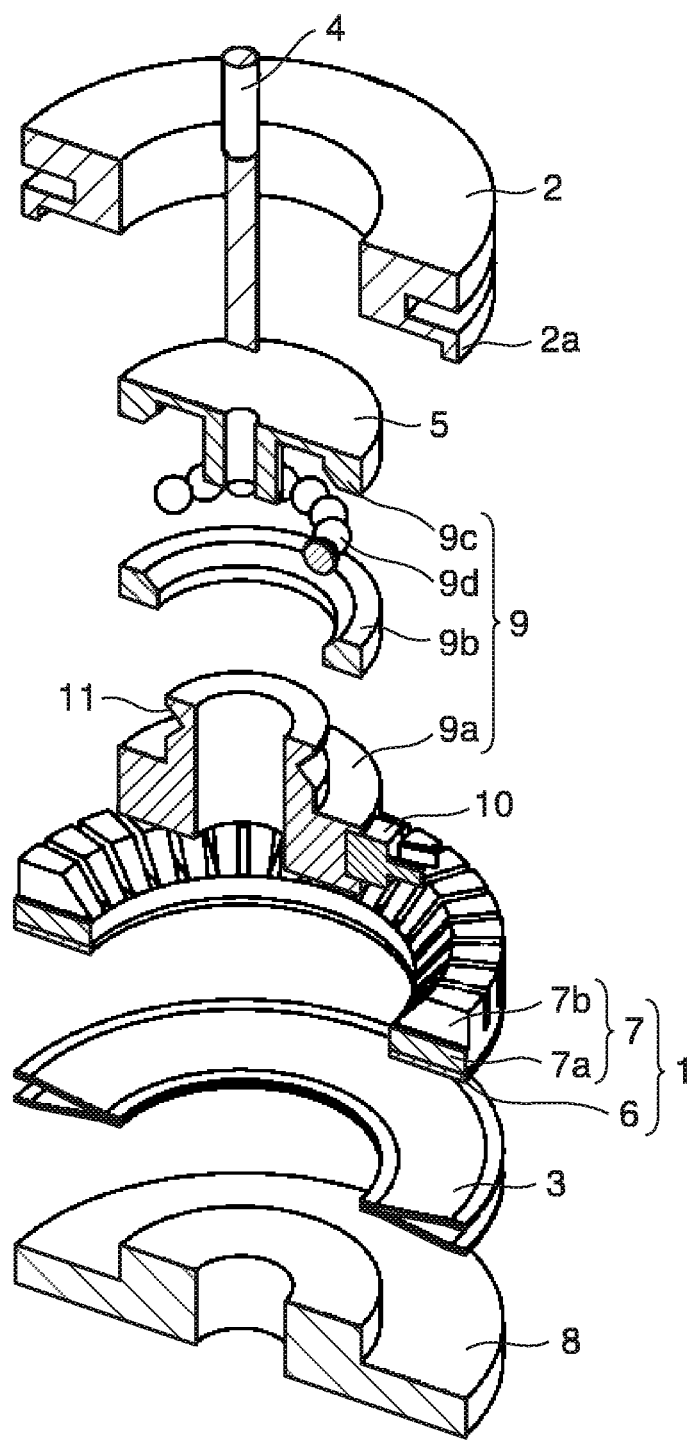
FIG. 2 is an exploded perspective view of the vibration drive device shown in FIGS. 1A and 1B, showing sections cut along a plane including a central axis of the vibration drive device in a thrust direction.

FIG. 1A is a schematic perspective view of a vibration drive device 100 according to a first embodiment of the present invention. FIG. 1B is a schematic cross-sectional view of the vibration drive device 100. FIG. 2 is an exploded perspective view of the vibration drive device 100 showing sections cut along a plane including a central axis, in a thrust direction. The vibration drive device 100 has a disk-like or columnar shape as a whole, and is comprised of a vibration element 1, a driven element 2, a pressure member 3, an output shaft 4, a driving force transmission member 5, a base 8, a bearing 9, and a rotation stopping member 10.

The vibration element 1 includes a piezoelectric element 6 which has an annular shape and an elastic body 7 which has an annular shape. The piezoelectric element 6, which is an electromechanical energy conversion element, is joined to the elastic body 7. By applying a predetermined AC voltage (driving voltage) to the piezoelectric element 6 using a well-known technique, it is possible to generate progressive vibration waves in the elastic body 7. The elastic body 7 is made of metal, such as stainless steel, and includes a base portion 7a which has an annular shape, and protrusions 7b formed on an upper surface of the base portion 7a (toward the driven element 2) at circumferentially equally-spaced intervals. The progressive vibration waves are formed on surfaces (upper surfaces) of the protrusions 7b, which are frictional sliding surfaces brought into frictional sliding contact with the driven element 2.

The rotation stopping member 10 protrudes in a radial direction (direction orthogonal to an axial direction of the output shaft 4) from a first bearing portion 9a, referred to hereinafter, fixed to the base 8 e.g. by an adhesive, and is inserted between adjacent ones of the protrusions 7b of the elastic body 7. With this arrangement, the vibration element 1 is attached to the base 8 in a manner unrotatable relative to the base 8, but movable in the thrust direction (direction parallel to the axial direction of the output shaft 4). The pressure member 3 is an urging unit for bringing the vibration element 1 and the driven element 2 into pressure contact with each other. In the illustrated example, an annular leaf spring is used as the pressure member 3. The pressure member 3 is arranged between the base 8 and the vibration element 1, and presses the vibration element 1 toward the driven element 2. With this arrangement, the upper surfaces of the protrusions 7b of the elastic body 7, which form an upper surface of the vibration element 1, is brought into pressure contact with a frictional sliding portion 2a, described hereinafter, which forms a lower surface of the driven element 2. As described above, the vibration drive device according to the first embodiment is configured to transmit progressive waves generated on the upper surface of each protrusion 7b to the frictional sliding portion 2a by friction, and hence it is preferable that the frictional sliding portion 2a and the protrusions 7b are each machined with high precision such that a shape can be ensured which is circumferentially low in undulation (high in flatness). To secure the high flatness, machining is performed by grinding using fixed abrasive grains, lapping or polishing using free abrasive grains, or the like.

The bearing 9 is a member for rotatably supporting the driven element 2. The bearing 9 includes a plurality of rolling elements 9d, the first bearing portion 9a, a second bearing portion 9b, and a third bearing portion 9c. Although in the first embodiment, each of the rolling elements 9d, the first bearing portion 9a, and the second bearing portion 9b is a single or separate component, the third bearing portion 9c is integrally formed with the driving force transmission member 5 from the same material.

A groove 11 having a V shape in cross-section is formed in an outer peripheral surface of the first bearing portion 9a. As described hereinafter, the rolling elements 9d receive the urging forces from a raceway surface of the second bearing portion 9b and a raceway surface of the third bearing portion 9c, whereby they are brought into contact with slopes of the groove 11. That is, the slopes of the groove 11 are used as a raceway surface (first raceway surface) on which the rolling elements 9d roll.

The second bearing portion 9b includes the raceway surface (second raceway surface) which has a fixed angle relative to the thrust direction, for allowing the rolling elements 9d to roll thereon. Further, the third bearing portion 9c includes the raceway surface (third raceway surface) which has a fixed angle relative to the thrust direction, for allowing the rolling elements 9d to roll thereon. The second bearing portion 9b and the third bearing portion 9c are fixed to the driven element 2 in a state where the raceway surfaces thereof are opposed to each other. More specifically, the second bearing portion 9b and the driving force transmission member 5 integrally formed with the third bearing portion 9c are fixed to the driven element 2 by an adhesive such that the second bearing portion 9b and the third bearing portion 9c are pressed against each other via the rolling elements 9d in an axial direction of the bearing 9 (the thrust direction). In other words, the second bearing portion 9b is fixed to the driven element 2 formed integrally i.e. as one piece, and the driving force transmission member 5 having the third bearing portion 9c is also fixed to the driven element 2 (a plurality of bearing portions are directly fixed to the driven element). In a case where the driven element 2 is formed by connecting or bonding a plurality of members (in a case where the driven element 2 is not formed integrally i.e. as one piece), even if the frictional sliding portion 2a is machined with high precision in a shape circumferentially low in undulation (high in flatness), there is a fear of degradation of flatness of the frictional sliding portion 2a due to connection or bonding of the plurality of members. As shown in the first embodiment, by forming the driven element including the frictional sliding portion 2a as a one-piece member (by integrally forming the same), it is possible to ensure the precision accuracy of the frictional sliding portion 2a. Further, in the first embodiment, the description is given of the case where the second bearing portion 9b and the driving force transmission member 5 including the third bearing portion 9c are directly fixed to the driven element 2 (in parallel with each other). With this arrangement in which the two members are fixed to the driven element 2, it is possible to make the mass and stiffness of the driven element 2 larger and the stability of driving performance against external disturbance higher than in a case where the two members are connected to the driven element in series such that one member is not in direct contact with the driven element 2. This because the following reasons: In a case where the two members are fixed to the driven element in series, with respect to the three members functioning as respective masses arranged in series, two fixing portions exist in the masses. In this state, the stiffness of each fixing portion is determined as a limited value, and hence as a mass is disposed at a more remote location from the driven element 2, the mass is difficult to function as an equivalent mass of the driven element 2. Therefore, by fixing the two members to the driven element 2 in parallel with each other, as in the first embodiment, it is possible to expect advantageous effects of increasing the equivalent mass of the driven element 2 and increasing the stability of driving performance against an external disturbance.

A force for pressing the second bearing portion 9b and the third bearing portion 9c via the rolling elements in the thrust direction is converted to a force for pressing the rolling elements 9d toward the output shaft 4 as the center of rotation by the raceway surfaces of the second bearing portion 9b and the third bearing portion 9c. Thus, the rolling elements 9d are pressed against the raceway surface of the first bearing portion 9a (the slopes of the groove 11) and are held in the state in pressure contact with the respective raceway surfaces of the first bearing portion 9a, the second bearing portion 9b, and the third bearing portion 9c. As described above, the stiffness of the bearing 9 is increased by eliminating play in the radial direction and the thrust direction, and hence it is possible to cause the driven element 2 to stably rotate without wobbling.

The driven element 2 includes the frictional sliding portion 2a having a spring property, for maintaining a proper contact state between the driven element 2 and the vibration element 1 by being deformed responsive to a vibration component which does not contribute to driving of the driven element 2 in a rotational direction, out of vibration components of driving vibration excited in the vibration element 1. Further, the frictional sliding portion 2a is frictionally driven by the progressive vibration waves formed on the upper surfaces of the protrusions 7b of the elastic body 7 as the upper surface of the vibration element 1, whereby the driven element 2 is driven for rotation about the axis of the output shaft 4. At this time, the rotational driving force of the driven element 2 is transmitted via the driving force transmission member 5 joined to the driven element 2 to the output shaft 4 joined to the driving force transmission member 5. This makes it possible to take out the rotational driving force from the output shaft 4 rotating according to the rotation of the driven element 2.

Here, in order for the frictional sliding portion 2a of the driven element 2 to properly maintain its spring property, it is required that the driven element 2 stably maintains its position and shape without being unnecessarily vibrated. As means for achieving this, there are generally employed a method of causing the driven element 2 to have sufficient mass, and a method of increasing the stiffness of the driven element 2 by increasing the cross-sectional shape of the vibration drive device 100 in the cross-section including the central axis in the thrust direction. With these methods, however, it is difficult to achieve reduction of the size and weight of the vibration drive device 100.

On the other hand, in the vibration drive device 100, the second bearing portion 9b and the third bearing portion 9c are fixed to the driven element 2 such that they are pressed via the rolling elements 9d against each other in the thrust direction, as mentioned above. By thus forming a preload mechanism in which the rolling elements 9d are brought into pressure contact with the respective raceway surfaces of the first, second, and third bearing portions 9a, 9b, and 9c, it is possible to increase the stiffness of the bearing 9. Further, the second bearing portion 9b and the third bearing portion 9c (integrally formed with the driving force transmission member 5) are bonded to the driven element 2 to thereby increase the stiffness of the driven element 2, whereby it is possible to suppress the displacement and deformation of the driven element 2 to stably hold the position and shape thereof. As a consequence, it is possible to obtain stable rotation performance by suppressing occurrence of unnecessary vibration of the driven element 2 without increasing the size thereof. In other words, the vibration drive device 100 is configured such that it is capable of compensating for insufficient stiffness of the driven element 2 using the stiffness of the bearing 9 formed integrally with the driven element 2, even though the stiffness of the driven element 2 itself is reduced by reducing the size and weight of the driven element 2.

Figure 3A:
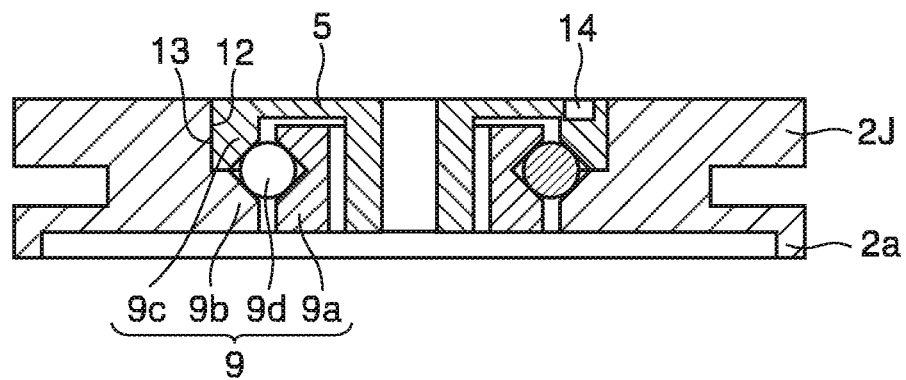
FIG. 3A is a schematic cross-sectional view of a driven element and a bearing as components of a vibration drive device according to a second embodiment of the present invention.
Figure 3B:
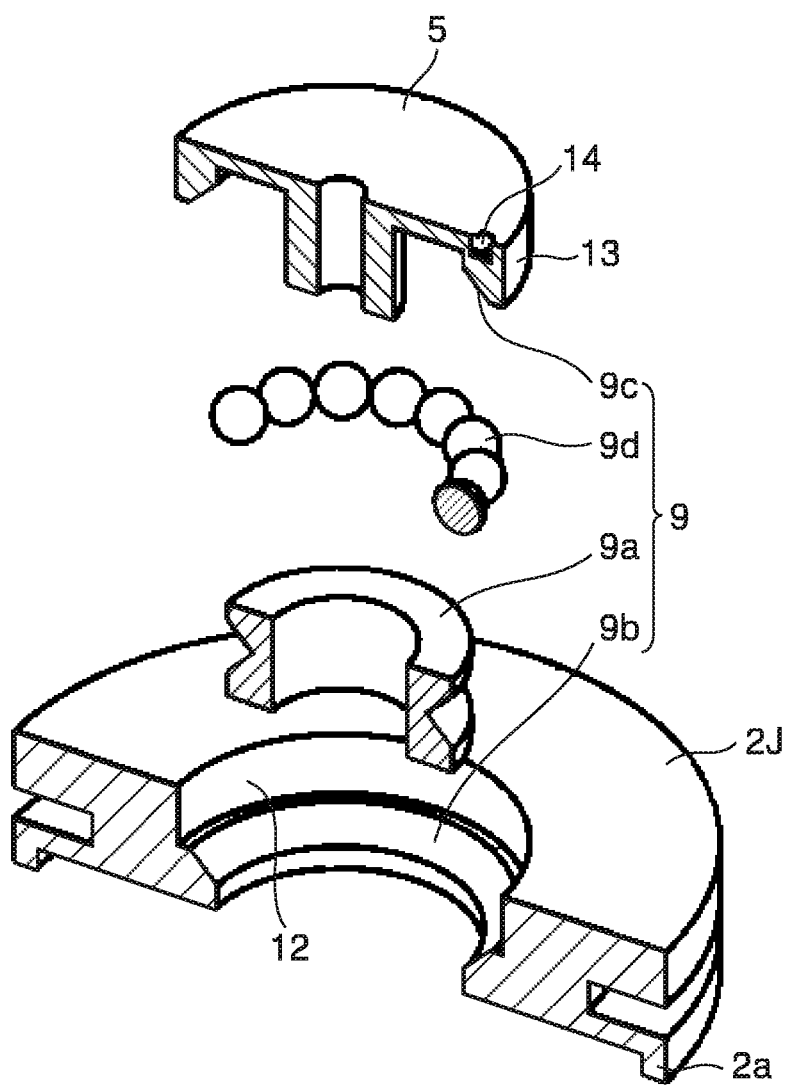
FIG. 3B is an exploded perspective view of the driven element and the bearing shown in FIG. 3A, showing sections cut along a plane including a central axis in a thrust direction.

FIG. 3A is a schematic cross-sectional view of a driven element 2J and the bearing 9 as components of a vibration drive device according to a second embodiment of the present invention. FIG. 3B is an exploded perspective view of the driven element 2J and the bearing 9 shown in FIG. 3A, showing sections cut along a plane including a central axis in a thrust direction. In the illustrated example, illustration of components common to those of the vibration drive device 100 according to the first embodiment is omitted, and description thereof is also omitted.

Although some corresponding components of each bearing are different between the first and second embodiments in that they are single parts or are integrally formed with other members, they are substantially the same in function, and hence the components forming the bearing are denoted by the same reference numerals. The same applies to third to sixth embodiments, described hereinafter. Note that although the first bearing portion 9a appearing in FIG. 2 is the same as in the first embodiment, illustration of part thereof toward the vibration element 1 is omitted, and also in each of the third to sixth embodiments, described hereinafter, illustration of part of the first bearing portion 9a toward the vibration element 1 is omitted.

The vibration drive device according to the second embodiment is largely distinguished from the vibration drive device 100 according to the first embodiment in the following two points: The first point is that the driven element 2J is formed by integrally forming the second bearing portion 9b and the driven element 2 as components of the vibration drive device 100 according to the first embodiment, from the same material. The second point is that the driving force transmission member 5 is mounted on the driven element 2J by threaded engagement.

In the vibration drive device 100 described in the first embodiment, the amplitude of vibration waves (driving vibration) generated on a frictional sliding surface of the vibration element 1 is as small as several microns. Therefore, it is an important factor for increasing the driving accuracy of the driven element 2, to bring the entire circumference of a lower surface (frictional sliding surface) of the frictional sliding portion 2a into uniform contact with the driving vibration, and efficiently convert the thrust of a rotational direction component of a driving force generated by the driving vibration to a driving force for driving the driven element 2 in the rotational direction thereof.

To bring the vibration element 1 and the driven element 2, which are described in the first embodiment, into uniform contact with each other over the entire circumference of the frictional sliding surface of the frictional sliding portion 2a, it is required not only that the planarity of the frictional sliding surface of the frictional sliding portion 2a is high but also that the surface deflection of the frictional sliding surface with respect to the rotation phase of the driven element 2 is small. Further, the deflection accuracy of the bearing 9 rotatably supporting the driven element 2 largely depends on the connected state (assembled state) of the bearing 9 and the driven element 2 and the construction of the bearing 9. Note that the deflection accuracy of the bearing 9 specifically refers to the accuracy of the raceway surfaces on which the rolling elements 9d roll, the position accuracy of each of the components of the bearing 9, the connection accuracy and position accuracy of the bearing 9 and the driven element 2.

In view of these circumstances, in the driven element 2J, the second bearing portion 9b and the frictional sliding portion 2a are concentrically formed by machining the same material in one chucking on a lathe. Therefore, in the driven element 2J, coaxiality of the frictional sliding portion 2a and the raceway surface of the second bearing portion 9b is very high, and further an angle of each of the frictional sliding surface of the frictional sliding portion 2a and the raceway surface of the second bearing portion 9b with respect to the thrust direction is also very high in accuracy. Therefore, in the vibration drive device using the driven element 2J having the second bearing portion 9b integrally formed therewith, the driven element 2J can be driven for rotation with higher accuracy than in the vibration drive device 100 according to the first embodiment. Further, the second bearing portion 9b which mainly receives a pressurization reaction force is formed as part of the driven element 2J, whereby it is increased in stiffness. This stabilizes the raceway surface of the second bearing portion 9b, whereby the driven element 2J can be stably driven for rotation with high accuracy even in a highly pressurized state.

Further, in the second embodiment as well, the third bearing portion 9c is integrally formed with the driving force transmission member 5. To this end, a female screw (not shown) is formed in an inner peripheral surface 12 of the driven element 2J, and a male screw (not shown) is formed on an outer peripheral surface 13 of the third bearing portion 9c. Then, by causing the female screw and the male screw to be threadedly engaged with each other, the driving force transmission member 5 and the driven element 2J are coupled to each other. In doing this, by adjusting fastening torque of the screws, it is possible to control the magnitude of the urging force applied from each of the respective raceway surfaces of the second bearing portion 9b and the third bearing portion 9c to the rolling elements 9d.

Further, by considering elastic deformation of each component of the bearing 9, the urging force received by the rolling elements 9d may be controlled by screwing the driving force transmission member 5 (the third bearing portion 9c) into the driven element 2J until abutment surfaces formed on the respective second and third bearing portion 9b and 9c are brought into contact with each other. FIG. 3A shows a state where the abutment surfaces of the second bearing portion 9b and the third bearing portion 9c are in contact with each other.

In the second embodiment, by forming screws (male and female screw) in the driven element 2J, the screws can be formed with a large number of turns in the thrust direction of the driven element 2J. This makes it possible to increase the stiffness of threadedly-engaged portions of the third bearing portion 9c and the driven element 2J, whereby it is possible to prevent degradation of shaft support performance e.g. due to looseness or deformation of the screws.

A hole 14 is formed at a location of an upper surface of the third bearing portion 9c (driving force transmission member 5). When the third bearing portion 9c is assembled to the driven element 2J, the third bearing portion 9c is fixed e.g. in a state where a pin or the like is inserted into the hole 14, and the driven element 2J is rotated such that the female screw formed in the inner peripheral surface 12 of the driven element 2J and the male screw formed on the outer peripheral surface 13 of the third bearing portion 9 are threadedly engaged with each other. This makes it possible to improve assembling workability, and further to easily adjust the magnitude of the urging force received by the rolling elements 9d from the respective raceway surfaces of the second bearing portion 9b and the third bearing portion 9c.

Note that the number of locations where the hole 14 is formed is not limited to one, but the hole 14 may be formed in a plurality locations. In this case, by using a jig provided with pins corresponding in number and location to the holes 14, it is possible to further improve the assembling workability. Further, this configuration may be replaced by a configuration in which a hole for the jig, similar to the hole 14, is formed in a lower surface (surface toward the vibration element 1) of the driven element 2J.

Figure 4A:
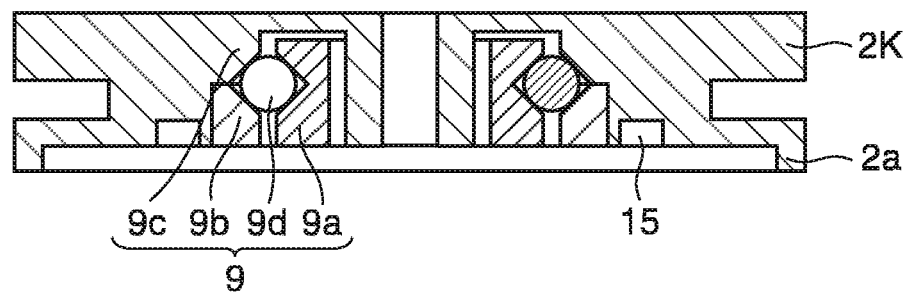
FIG. 4A is a schematic cross-sectional view of a driven element and a bearing as components of a vibration drive device according to a third embodiment of the present invention.
Figure 4B:
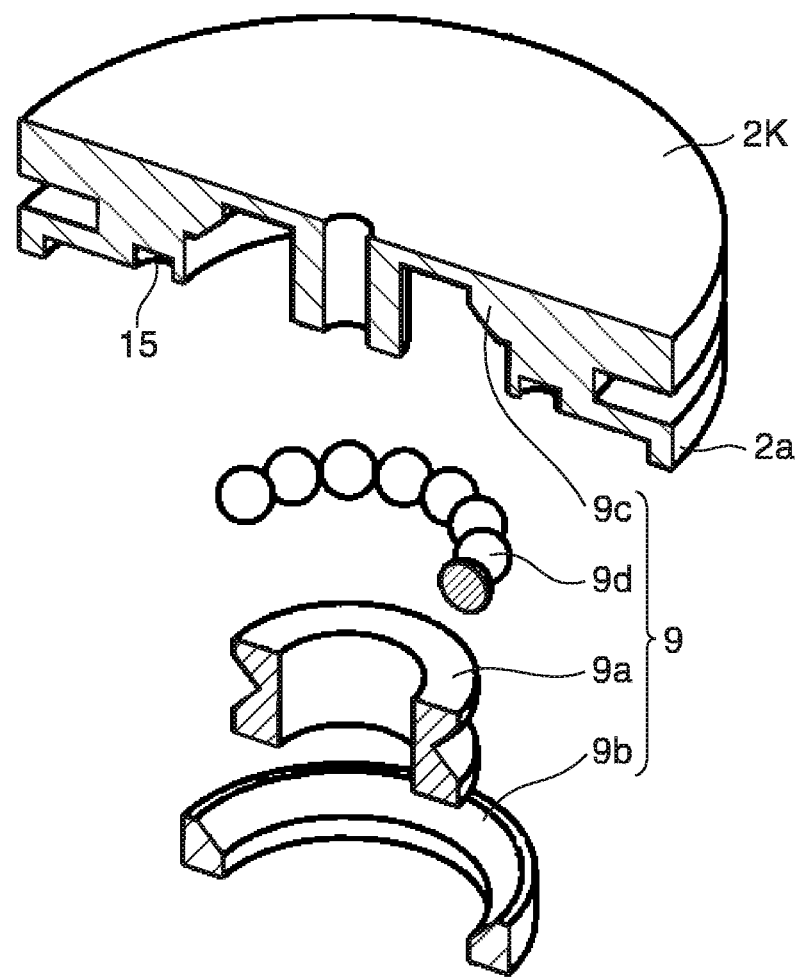
FIG. 4B is an exploded perspective view of the driven element and the bearing shown in FIG. 4A, showing sections cut along a plane including a central axis in a thrust direction.

FIG. 4A is a schematic cross-sectional view of a driven element 2K and a bearing 9 as components of a vibration drive device according to a third embodiment of the present invention. FIG. 4B is an exploded perspective view of the driven element 2K and the bearing 9 shown in FIG. 4A, showing sections cut along a plane including a central axis in a thrust direction. In this example as well, illustration of components common to those of the vibration drive device 100 according to the first embodiment is omitted, and description thereof is also omitted.

The vibration drive device according to the third embodiment is largely distinguished from the vibration drive device 100 according to the first embodiment in the following two points: The first point is that the driven element 2K is formed by integrally forming the third bearing portion 9c, the driving force transmission member 5, and the driven element 2 as components of the vibration drive device 100 according to the first embodiment, from the same material. The second point is that the second bearing portion 9b is held in a state in contact with the third bearing portion 9c by being press-fitted into the driven element 2K.

In the driven element 2K, similar to the driven element 2J described in the second embodiment, by machining the same material in one chucking on a lathe, it is possible to concentrically form the third bearing portion 9c and the frictional sliding portion 2a. This stabilizes the raceway surface of the third bearing portion 9c, whereby it is possible to stably drive the driven element 2K for rotation with high accuracy even in a highly pressurized state.

The sizes of abutment portions formed on the second bearing portion 9b and the third bearing portion 9c, respectively, can be set by taking into account elastic deformation due to a force with which the second and third bearing portions 9b and 9c are pressed against each other via the rolling elements 9d. When assembling, it is possible to form a desired preload mechanism by press-fitting the second bearing portion 9b to the third bearing portion 9c until the abutment portion of the second bearing portion 9b is brought into contact with the abutment portion of the third bearing portion 9c.

Figure 5A:
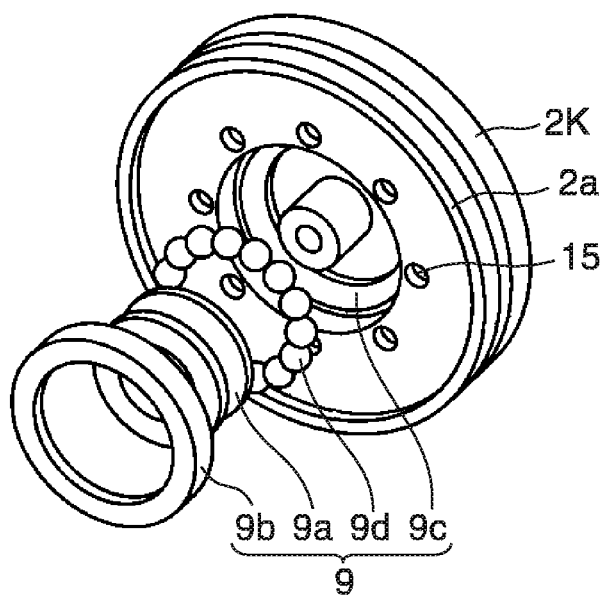
FIGS. 5A to 5C are perspective views of the driven element and the bearing shown in FIGS. 4A and 4B, corresponding to respective stages of assembly.
Figure 5B:
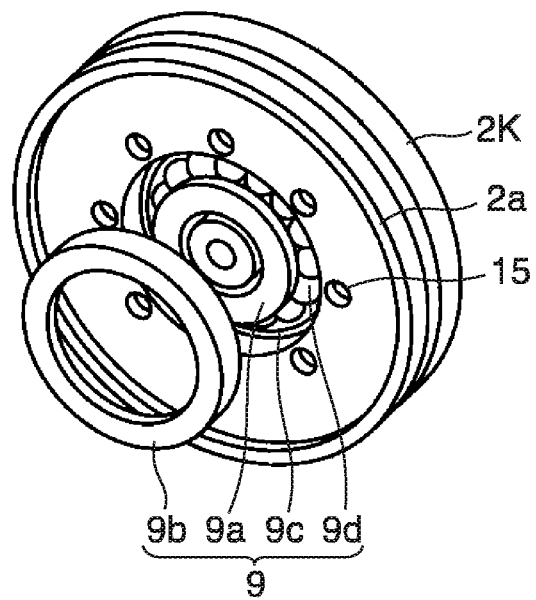
Figure 5C:
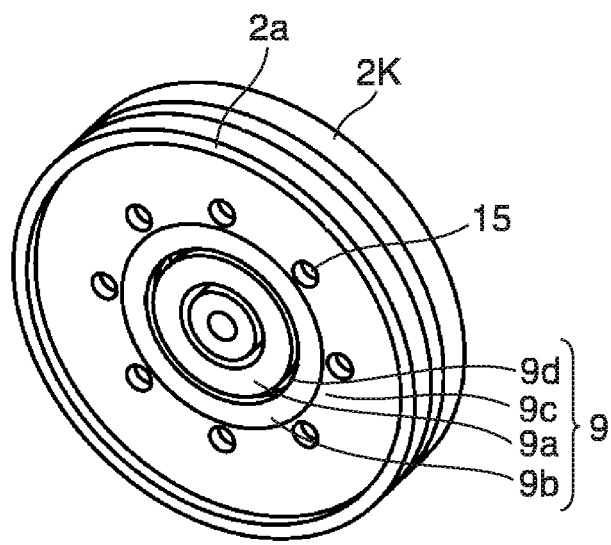

FIGS. 5A to 5C are perspective views of the driven element 2K and the bearing 9 shown in FIGS. 4A and 4B, corresponding to respective stages of assembly. FIG. 5A is an exploded perspective view of the driven element 2K and the bearing 9, as viewed from a direction different from a direction in which they are viewed in FIG. 4B. FIG. 5B is a perspective view of the driven element 2K and the bearing 9 in a state where the first bearing portion 9a and the rolling elements 9d are disposed on the driven element 2K before the second bearing portion 9b is press-fitted into the driven element 2K. FIG. 5C is a perspective view of the driven element 2K and the bearing 9 in a state where the press-fitting of the second bearing portion 9b into the driven element 2K has been completed (perspective view showing the same state as shown in FIG. 4A). It is understood from FIGS. 5A to 5C that the driven element 2K and the bearing 9 can be very easily assembled to each other.

There are formed a plurality of holes 15 in the vicinity of an inner-diameter side of a lower surface of the driven element 2K into which the second bearing portion 9b is press-fitted. The holes 15 have a function of absorbing a force which expands the driven element 2K radially outward by a press-fitting reaction force, to thereby prevent deformation of the frictional sliding portion 2a of the driven element 2K. The shape of each hole 15 is not limited to a circular shape, but it may be a rectangular shape or an elliptical shape. Further, the holes 15 may be replaced by a circumferential groove formed concentrically with an outer periphery of the driven element 2K.

Note that the bearing 9 may be formed by assembling the second bearing portion 9b to the driven element 2K by loose-fitting instead of press-fitting. In this case, fitting portions of the second bearing portion 9b and the driven element 2K may be fixed to each other by an adhesive in a state in which the second bearing portion 9b is urged against the third bearing portion 9c of the driven element 2K in the thrust direction.

In the second embodiment, the second bearing portion 9b and the driven element 2 are integrally formed with each other, and in the third embodiment, the third bearing portion 9c and the driven element 2 are integrally formed with each other. In doing this, by forming a member having a larger cross-sectional shape, out of the second bearing portion 9b and the third bearing portion 9c, integrally with the driven element 2, it is possible, even with the same configuration, to impart a larger mass and a higher stiffness to the driven element 2 to thereby stabilize the driving characteristics thereof.

Figure 6A:
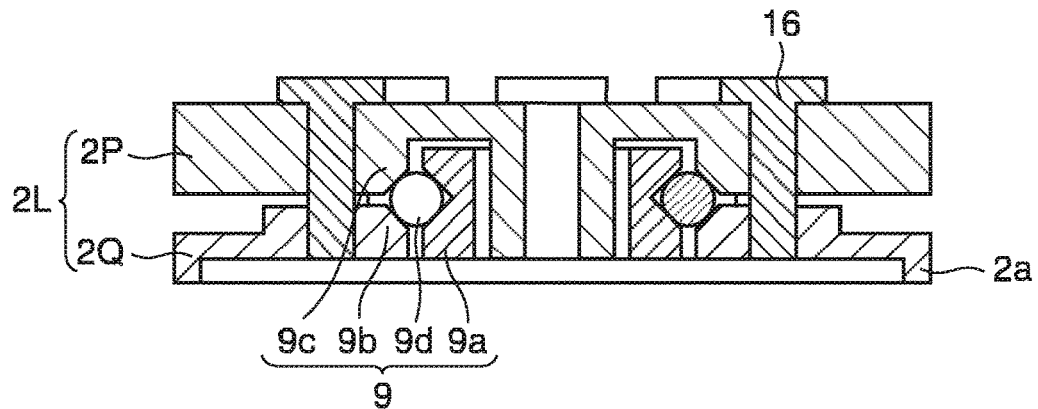
FIG. 6A is a schematic cross-sectional view of a driven element and a bearing as components of a vibration drive device according to a fourth embodiment of the present invention.
Figure 6B:
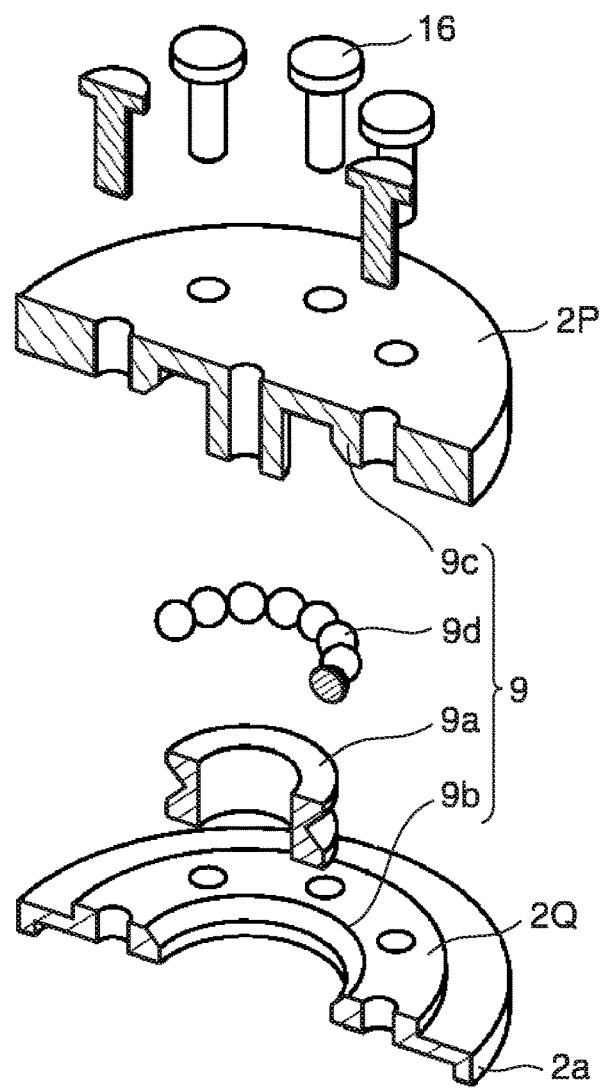
FIG. 6B is an exploded perspective view of the driven element and the bearing shown in FIG. 6A, showing sections cut along a plane including a central axis in a thrust direction.

FIG. 6A is a schematic cross-sectional view of a driven element 2L and a bearing 9 as components of a vibration drive device according to a fourth embodiment of the present invention. FIG. 6B is an exploded perspective view of the driven element 2L and the bearing 9 shown in FIG. 6A, showing sections cut along a plane including a central axis in a thrust direction. In this example as well, illustration of components common to those of the vibration drive device 100 according to the first embodiment is omitted, and description thereof is also omitted.

The driven element 2L according to the fourth embodiment has a structure in which a first component 2P and a second component 2Q are coupled to each other with bolts 16 in the thrust direction. The first component 2P has a structure in which part of the driven element 2 described in the first embodiment, and the driving force transmission member 5 and the third bearing portion 9c which are described in the same, are integrally formed from the same material. The second component 2Q has a structure in which part of the driven element 2 described in the first embodiment, and the frictional sliding portion 2a and the second bearing portion 9b which are described in the same, are integrally formed from the same material.

In the course of a process of fastening the first component 2P and the second component 2Q with the bolts 16, the rolling elements 9d are brought into contact with the raceway surfaces of the second bearing portion 9b and the third bearing portion 9c, and are pressed against the raceway surface of the first bearing portion 9a, whereby positions where the rolling elements 9d are arranged are restricted. In doing this, by performing fastening of a pair of bolts 16 opposed to each other with the center of rotation of the driven element 2L positioned therebetween, i.e. so-called opposed fastening, it is possible to perform centering of the axis of the second and third bearing portions 9b and 9c with respect to the first bearing portion 9a. Thus, it is possible to realize high-accuracy shaft support. Further, it is easy to assemble the driven element 2L and the bearing 9 since it is only requited to fasten the first and second components 2P and 2Q with the bolts 16 in a state in which all these components are assembled thereto.

Figure 7A:
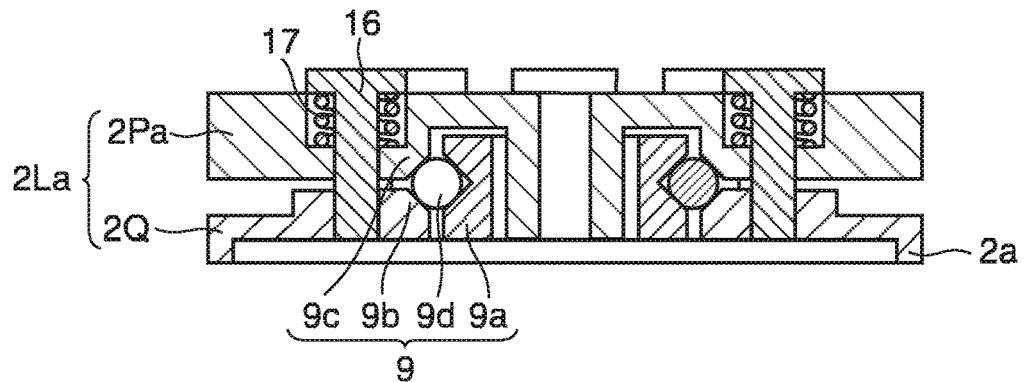
FIG. 7A is a schematic cross-sectional view of a driven element and a bearing as components of a vibration drive device according to a fifth embodiment of the present invention.
Figure 7B:
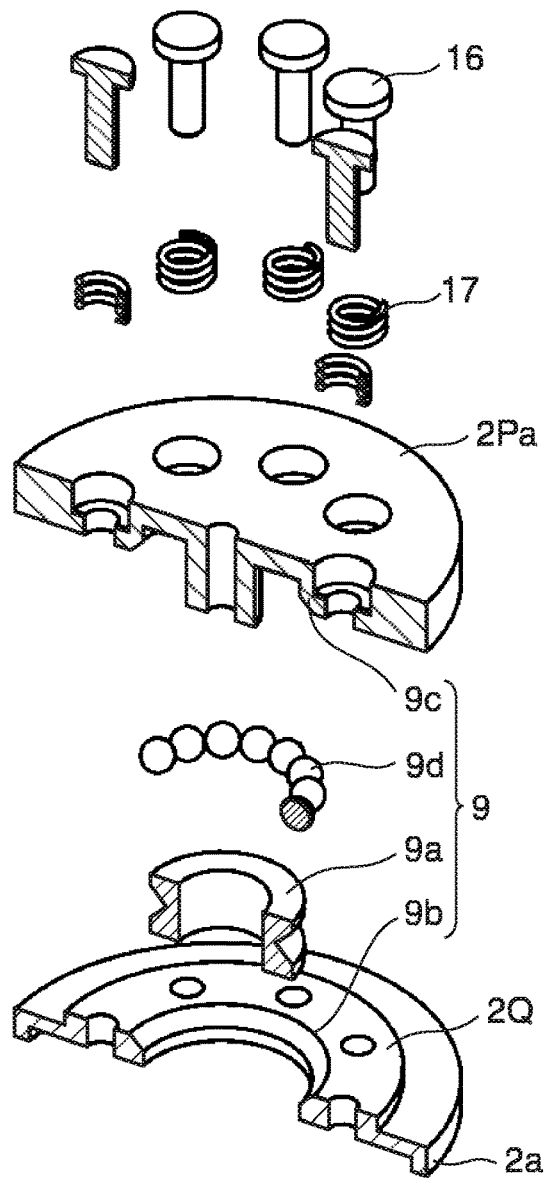
FIG. 7B is an exploded perspective view of the driven element and the bearing shown in FIG. 7A, showing sections cut along a plane including a central axis in a thrust direction.

In a fifth embodiment, there is used a first variation of the driven element 2L which is a component of the vibration drive device according to the fourth embodiment. FIG. 7A is a schematic cross-sectional view of a driven element 2La and a bearing 9 as components of a vibration drive device according to the fifth embodiment of the present invention. FIG. 7B is an exploded perspective view of the driven element 2La and the bearing 9 shown in FIG. 7A, showing sections cut along a plane including a central axis in a thrust direction.

The driven element 2La as the first variation of the driven element 2L is configured such that a first component 2Pa and the second component 2Q are fastened to each other with the bolts 16 in a state where the bolts 16 are inserted through coil springs 17. The first component 2Pa has a structure in which the first component 2P, described in the fourth embodiment, has holes, through which the bolts 16 are inserted, increased in diameter, such that the coil springs 17 can be arranged therein. The second component 2Q is the same as the second component 2Q, described in the fourth embodiment.

In general, a bearing operates while receiving repeated stress due to rolling of the rolling elements on raceway surfaces of an outer ring and an inner ring of the bearing, and the magnitude of the repeated stress is a large factor in determining the service life of the bearing. Therefore, by adjusting the amount of deformation (compression) of the coil springs 17 using a fastening structure in which the coil springs 17 are disposed therein, it is possible to finely set a force with which the second bearing portion 9b and the third bearing portion 9c are pressed against each other in the thrust direction. This makes it possible to stably control an internal preload force which determines the repeated stress of the bearing 9 dependent on a time period over which the vibration drive device is in use.

Figure 8A:
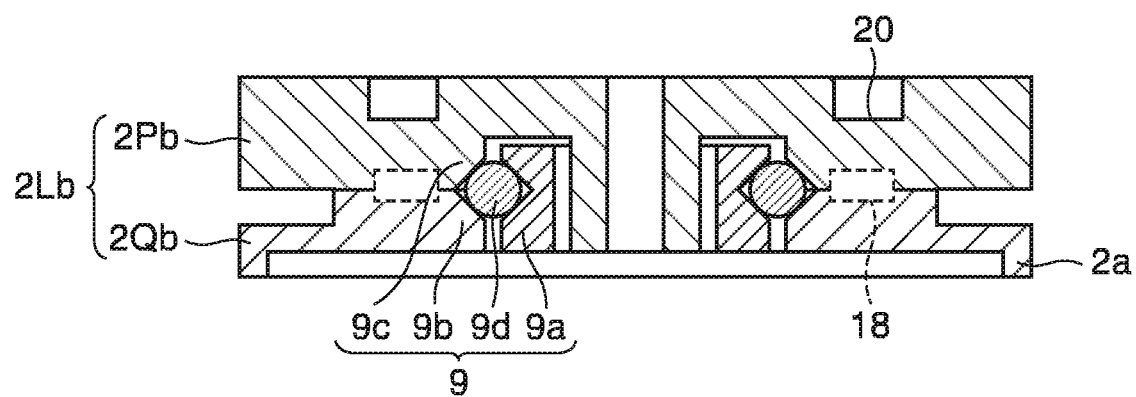
FIG. 8A is a schematic cross-sectional view of a driven element and a bearing as components of a vibration drive device according to a sixth embodiment of the present invention.

In a sixth embodiment, there is used a second variation of the driven element 2L which is a component of the vibration drive device according to the fourth embodiment. FIG. 8A is a schematic cross-sectional view of a driven element 2Lb and a bearing 9 as components of a vibration drive device according to the sixth embodiment of the present invention. The driven element 2Lb as the second variation of the driven element 2L has a structure in which a first component 2Pb and a second component 2Qb are joined to each other by electric resistance welding in a welded area 18.

Figure 8B:
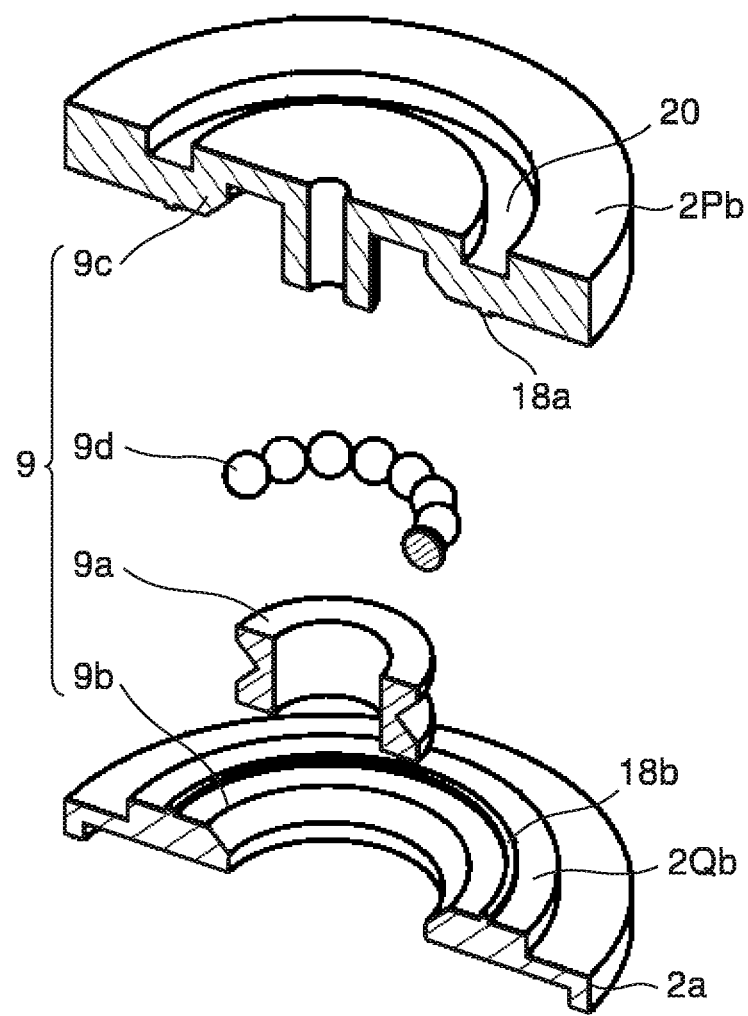
FIG. 8B is an exploded perspective view of the driven element and the bearing shown in FIG. 8A, showing sections cut along a plane including a central axis in a thrust direction.

FIG. 8B is an exploded perspective view of the driven element 2Lb and the bearing 9 shown in FIG. 8A, showing sections cut along a plane including a central axis in a thrust direction. However, FIG. 8B shows a state of the components of the driven element 2Lb and the bearing 9 before the first and second components 2Pb and 2Qb are joined to each other by electric resistance welding. The first component 2Pb has a structure in which the first component 2P, described in the fourth embodiment, is provided with an annular groove 20 for having one of a pair of electrodes 19, referred to hereinafter, disposed therein for performing electric resistance welding, and an annular protrusion 18a which melts during electric resistance welding. The second component 2Qb has a structure in which the second component 2Q, described in the fourth embodiment, is provided with an annular protrusion 18b which melts during electric resistance welding.

Figure 9A:
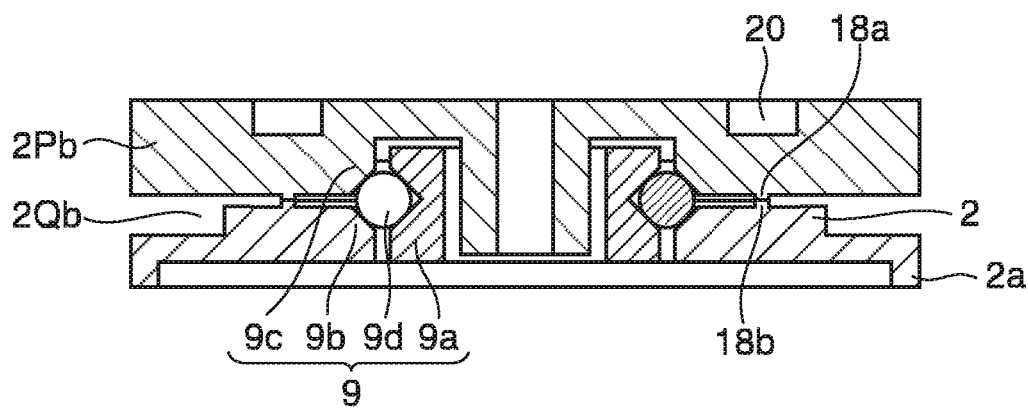
FIGS. 9A and 9B are views useful in explaining a process for performing electric resistance welding of a first component and a second component appearing in FIGS. 8A and 8B.
Figure 9B:
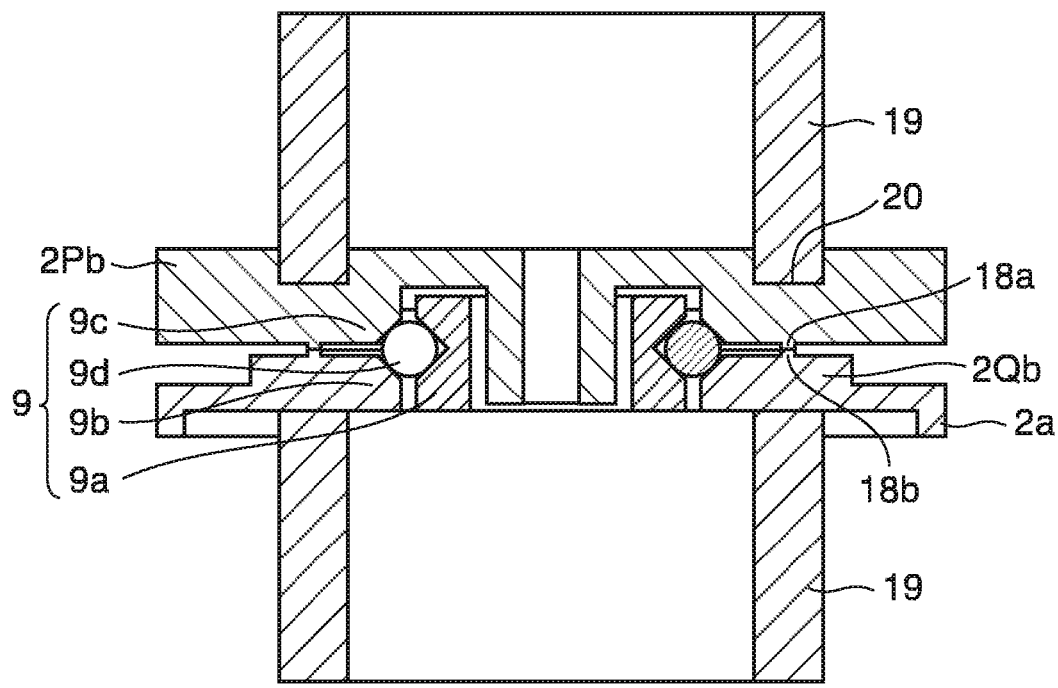

FIGS. 9A and 9B are views useful in explaining a process of electric resistance welding performed on the first component 2Pb and the second component 2Qb. FIG. 9A is a cross-sectional view of a state of arrangement of the first component 2Pb and the second component 2Qb before executing electric resistance welding. FIG. 9B is a diagram showing a state in which the electrodes 19 each having a hollow cylindrical shape are disposed on the first component 2Pb and the second component 2Qb shown in FIG. 9A, respectively.

As shown in FIG. 9A, the first and second components 2Pb and 2Qb are set such that they contain the first bearing portion 9a and the rolling elements 9d. At this time, the annular protrusions 18a and 18b are roughly brought into abutment with each other. Next, the first and second components 2Pb and 2Qb shown in FIG. 9A are caught between the pair of electrodes 19 of a resistor, as shown in FIG. 9B, and are coaxially arranged such that the annular protrusions 18a and 18b are brought into abutment with each other. Then, the first and second components 2Pb and 2Qb are held in a pressurized state with a predetermined force in the thrust direction.

Then, a current is caused to flow between the electrodes 19 opposed to each other via the first and second components 2Pb and 2Qb. At this time, the current is concentrated on the annular protrusions 18a and 18b, and a local temperature rise caused by heat generation due to electric resistance melts the annular protrusions 18a and 18b, whereby a lower surface of the first component 2Pb and an upper surface of the second component 2Qb are brought into close contact with each other. By stopping application of the current after melting the annular protrusions 18a and 18b, melted portions of the annular protrusions 18a and 18b are solidified, whereby the welded area 18 appearing in FIG. 8A is formed, and the first and second components 2Pb and 2Qb are joined to each other. At this time, the welded area 18 is formed in a state where the first and second components 2Pb and 2Qb are pressurized by the electrodes 19, and hence the state is maintained in which the rolling elements 9d are pressed against the raceway surface of the first bearing portion 9a by the respective raceway surfaces of the second and third bearing portions 9b and 9c.

Note that the first component 2Pb and the second component 2Qb are formed of e.g. a metal material, such as an austenitic stainless steel, which has a large electric resistance. On the other hand, the rolling elements 9d are made of a non-conductive material, such as tungsten carbide or zirconia. Therefore, during electric resistance welding, an electric path via the rolling elements 9d is insulated, and a current (electric path) is concentrated on the annular protrusions 18a and 18b which should be welded, whereby it is possible to efficiently weld the annular protrusions 18a and 18b at a desired position. Although in the illustrated example, the first and second components 2Pb and 2Qb are provided with the annular protrusions 18a and 18b, respectively, only one of the first and second components 2Pb and 2Qb may be provided with an annular protrusion. Further, the annular protrusions may be replaced by island-shaped protrusions in discrete arrangement.

Incidentally, when electric resistance welding is performed, if respective distances from the two electrodes 19 to the contact surfaces of the annular protrusions 18a and 18b as welding positions are different, there is a fear that the temperature of a welding portion does not rise to a sufficiently high melting temperature, which makes it impossible to obtain a desired welding quality. One solution to this problem is a method of changing the sizes of the two electrodes 19 for adjustment such that the temperature of the welding portion reaches the sufficiently high melting temperature. However, this method suffers from a problem that it is difficult to control the electrode characteristics with time due to occurrence of a difference between degrees of wear of the two electrodes 19. Therefore, it is idealistic that the respective distances from the two electrodes 19 to the welded portion are made equal to each other. Further, in electric resistance welding, it is desirable to shorten spacing between the electrodes since a voltage which should be applied for welding is reduced as the current flows through the first and second components 2Pb and 2Qb as objects to be welded.

To this end, in the sixth embodiment, the annular groove 20 is formed in the first component 2Pb, and one of the electrodes 19 is inserted into the annular groove 20, whereby a distance from the electrode 19 to the end face of the annular protrusion 18a is shortened. More specifically, a distance between the annular protrusion 18b formed on the second component 2Qb and the electrode 19 so disposed as to be brought into contact with the second component 2Qb, and a distance between the annular protrusion 18a formed on the first component 2Pb and the electrode 19 so disposed as to be inserted into the annular groove 20 are made substantially equal to each other.

Note that the method of welding the first component 2Pb and the second component 2Qb is not limited to electric resistance welding, but they may be welded to each other by arc welding or laser welding. In such a case, the annular protrusions 18a and 18b are not formed, but portions of the first and second components 2Pb and 2Qb at a location close to the outer periphery of a contact area therebetween form welding portions.

Figure 10A:
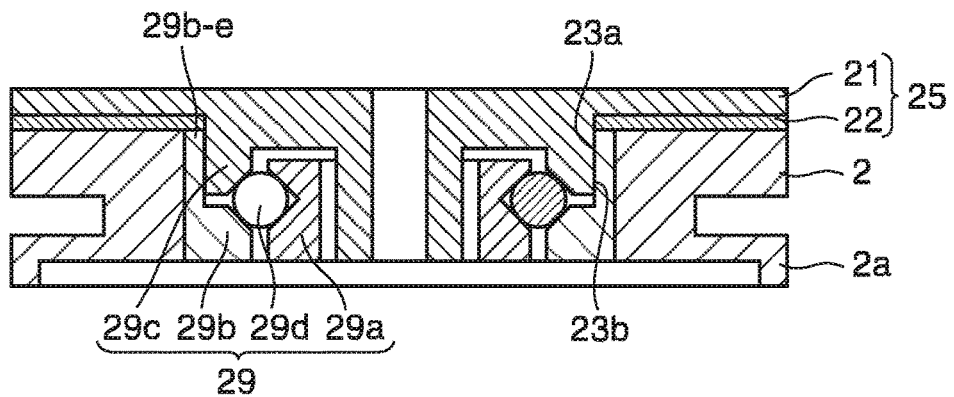
FIG. 10A is a schematic cross-sectional view of a driven element, a bearing, and a driving force transmission member as components of a vibration drive device according to a seventh embodiment of the present invention.
Figure 10B:
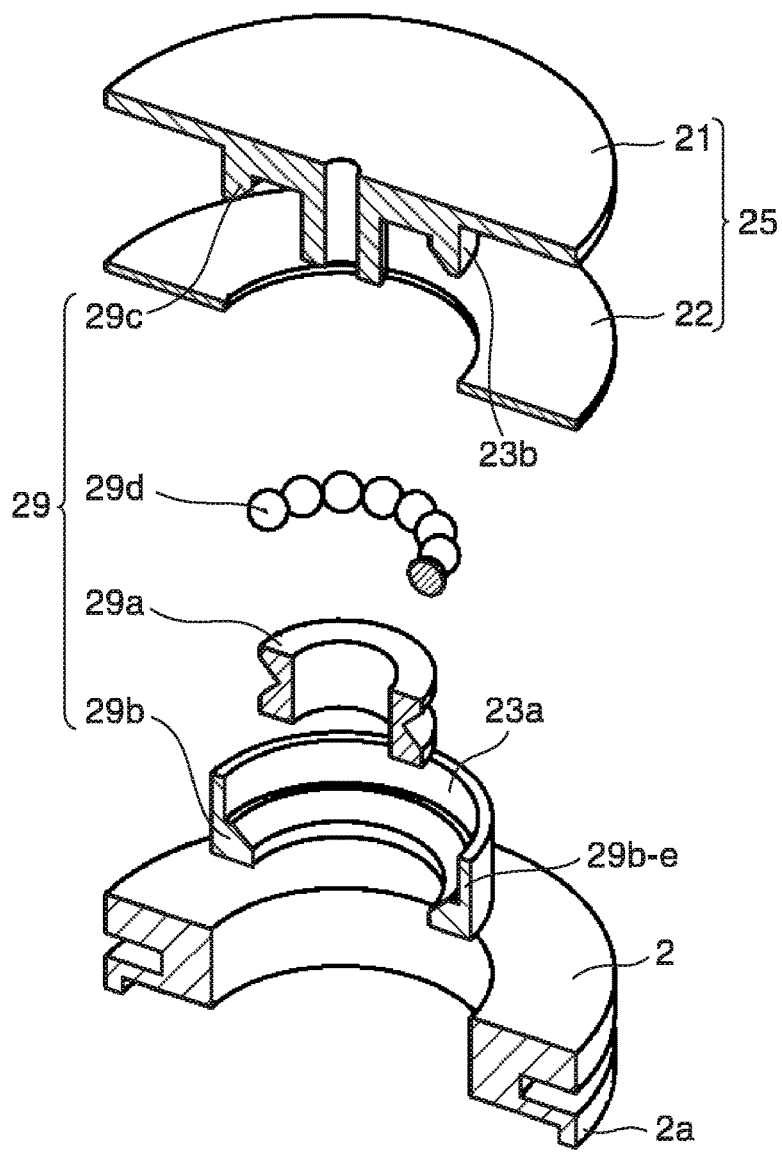
FIG. 10B is an exploded perspective view of the bearing and the driving force transmission member shown in FIG. 10A, showing sections cut along a plane including a central axis in a thrust direction.

In a seventh embodiment, there are used respective variations of the bearing 9 and the driving force transmission member 5 which are described in the first embodiment. FIG. 10A is a schematic cross-sectional view of a driven element 2, a bearing 29, and a driving force transmission member 25 as components of a vibration drive device according to the seventh embodiment of the present invention. FIG. 10B is an exploded perspective view of the driven element 2, the bearing 29, and the driving force transmission member 25 shown in FIG. 10A, showing sections cut along a plane including a central axis in a thrust direction. In this example as well, illustration of components common to those of the vibration drive device 100 according to the first embodiment is omitted, and description thereof is also omitted.

The driven element 2 is the same as described in the first embodiment. The bearing 29 includes a plurality of rolling elements 29d, a first bearing portion 29a, a second bearing portion 29b, and a third bearing portion 29c. The driving force transmission member 25 includes a flange 21 and an annular plate-shaped rubber member 22.

The rolling elements 29d and the first bearing portion 29a are the same as the rolling elements 9d and the first bearing portion 9a forming the bearing 9 in the first embodiment. Illustration of part of the first bearing portion 29a toward the vibration element 1 (not shown) is omitted. The second bearing portion 29b has an extended portion 29b-e extended from the outer periphery thereof in the thrust direction, and the extended portion 29b-e has an inner peripheral surface thereof formed with a female screw 23a. The third bearing portion 29c is integrally formed with the flange 21, as part of the flange 21, from the same material. The third bearing portion 29c has an outer peripheral surface thereof formed with a male screw 23b which is threadedly engaged with the female screw 23a of the second bearing portion 29b.

Assembly of the components shown in FIGS. 10A and 10B are performed as follows: First, the first bearing portion 29a is disposed in the third bearing portion 29c, and then a predetermined number of the rolling elements 29d are disposed in a raceway. Then, the rubber member 22 is disposed on a surface of the flange 21, which is formed with the third bearing portion 29c. Note that although in general, the inner diameter of the rubber member 22 is equal to the outer diameter of the third bearing portion 29c, it is set to such a value that an inner peripheral side of the rubber member 22 is not lifted from the flange 21.

Subsequently, the second bearing portion 29b is threadedly engaged with the third bearing portion 29c while adjusting a fastening torque, whereby a force with which the second bearing portion 29b and the third bearing portion 29c are pressed against each other via the rolling elements 9d in the thrust direction is controlled to a predetermined value. Next, the driven element 2 having an inner peripheral surface thereof coated with an adhesive is fitted on the second bearing portion 29b, and the adhesive existing between the inner peripheral surface of the driven element 2 and an outer peripheral surface of the second bearing portion 29b is cured in a state in which a surface of the driven element 2 toward the flange 21 is brought into contact with the rubber member 22. This completes the assembly.

After the assembly, the flange 21 and the driven element 2 are coupled to each other such that they are caused to rotate in unison with each other by the frictional force of the rubber member 22 (in other words, they cannot rotationally move relative to each other). Further, the second bearing portion 29b is bonded to the driven element 2. Therefore, the second bearing portion 29b and the third bearing portion 29c rotate in the same direction following the rotation of the driven element 2, and are not changed in position relative to each other. This prevents threadedly-engaged portions of the second and third bearing portions 29b and 29c from being loosened. Therefore, the stiffness of the bearing 29 is not degraded due to occurrence of loosening of the threadedly-engaged portions of the second and third bearing portions 29b and 29c.

Further, even when the flange 21 is thin and it is difficult to ensure plane accuracy, the adverse influence of a low planarity of the flange 21 is mitigated by the rubber member 22 and hence it is possible to maintain the planarity of the frictional sliding portion 2a, which is high-precision machined, of the driven element 2. Furthermore, an upper surface of the flange 21 can be used as a take-out surface for taking out a rotational output. In this case, an external force applied to the flange 21 is reduced by the rubber member 22, whereby it is possible to prevent the external force from directly acting on the driven element 2. This makes it possible to maintain a stable contact state between the driven element 2 and the vibration element 1.

Figure 11:
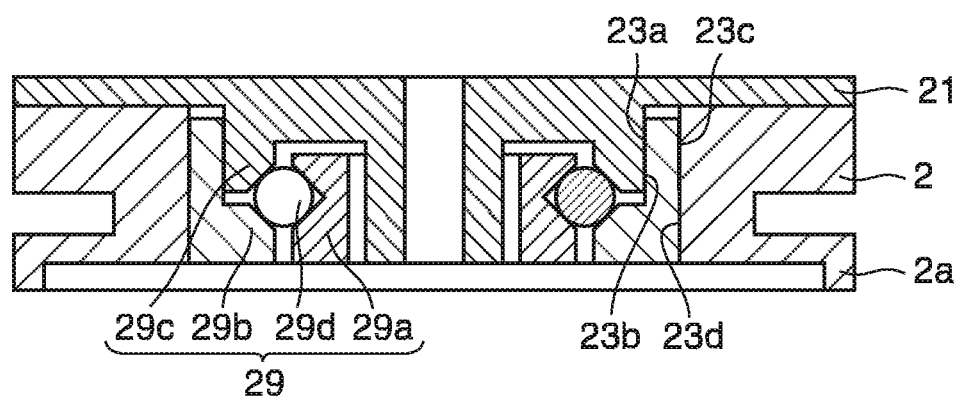
FIG. 11 is a cross-sectional view of an assembled state of a driven element, a bearing, and a flange as components of a vibration drive device according to an eighth embodiment of the present invention.

FIG. 11 is a cross-sectional view of a driven element 2, a bearing 29, and a flange 21 as components of a vibration drive device according to an eighth embodiment of the present invention. In the illustrated example, illustration of components common to those of the vibration drive device 100 according to the first embodiment is omitted, and description thereof is also omitted. Further, although the bearing of the present embodiment is partially different from the bearing 29 described in the seventh embodiment due to a difference in the assembly method, they have the same basic configuration, and hence the same components as those of the bearing 29 described in the seventh embodiment are denoted by the same reference numerals, and description thereof is omitted. The same applies to a ninth embodiment and a tenth embodiment, described hereinafter.

The flange 21 is the same as described in the seventh embodiment. The extended portion 29b-e of the second bearing portion 29b has an outer peripheral surface thereof formed with a male screw 23c. The inner peripheral surface of the driven element 2 is formed with a female screw 23d which is threadedly engaged with the male screw 23c of the second bearing portion 29b. In these points, the eighth embodiment differs from the seventh embodiment.

To assemble the driven element 2, the bearing 29, and the flange 21 to each other, first, the first bearing portion 29a is disposed in the third bearing portion 29c. Then, a predetermined number of the rolling elements 29d are disposed in a raceway, and the second bearing portion 29b is threadedly engaged with the third bearing portion 29c while adjusting a fastening torque. With this, similar to the seventh embodiment, a force with which the second bearing portion 29b and the third bearing portion 29c are pressed against each other via the rolling elements 9d in the thrust direction is controlled to a predetermined value.

Subsequently, the driven element 2 is threadedly engaged with the second bearing portion 29b until the driven element 2 is brought into contact with the flange 21. At this time, the contact surfaces of the flange 21 and the driven element 2 are joined to each other e.g. by an adhesive. As a consequence, the flange 21 and the driven element 2 are joined such that they cannot rotationally move relative to each other. Therefore, similar to the seventh embodiment, the stiffness of the bearing 29 is prevented from being degraded by occurrence of loosening of the threadedly-engaged portions of the second and third bearing portions 29b and 29c.

Note that the female screw 23a and the male screw 23c of the second bearing portion 29b can be formed by simultaneous machining, whereby it is possible to perform centering of a central axis thereof with high accuracy. Therefore, the second bearing portion 29b, the flange 21, and the driven element 2 can be threadedly engaged with each other along the central axis thereof with high accuracy, thereby making it possible to cause the driven element 2 to stably rotate without wobbling.

Figure 12A:
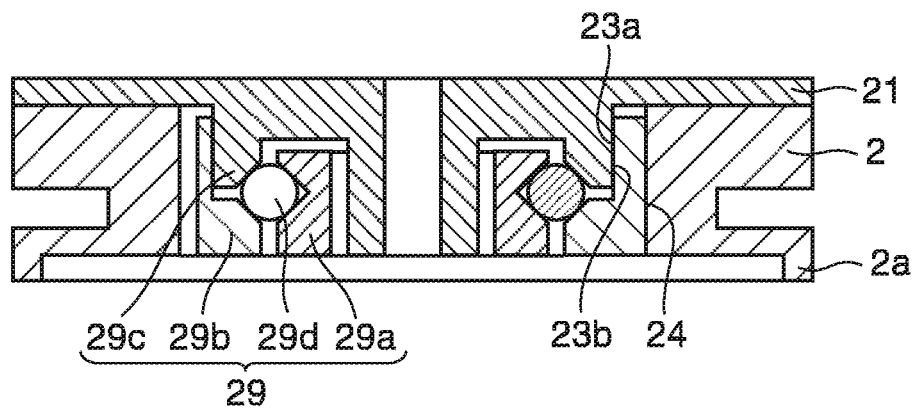
FIG. 12A is a cross-sectional view of an assembled state of a driven element, a bearing, and a flange as components of a vibration drive device according to a ninth embodiment of the present invention.
Figure 12B:
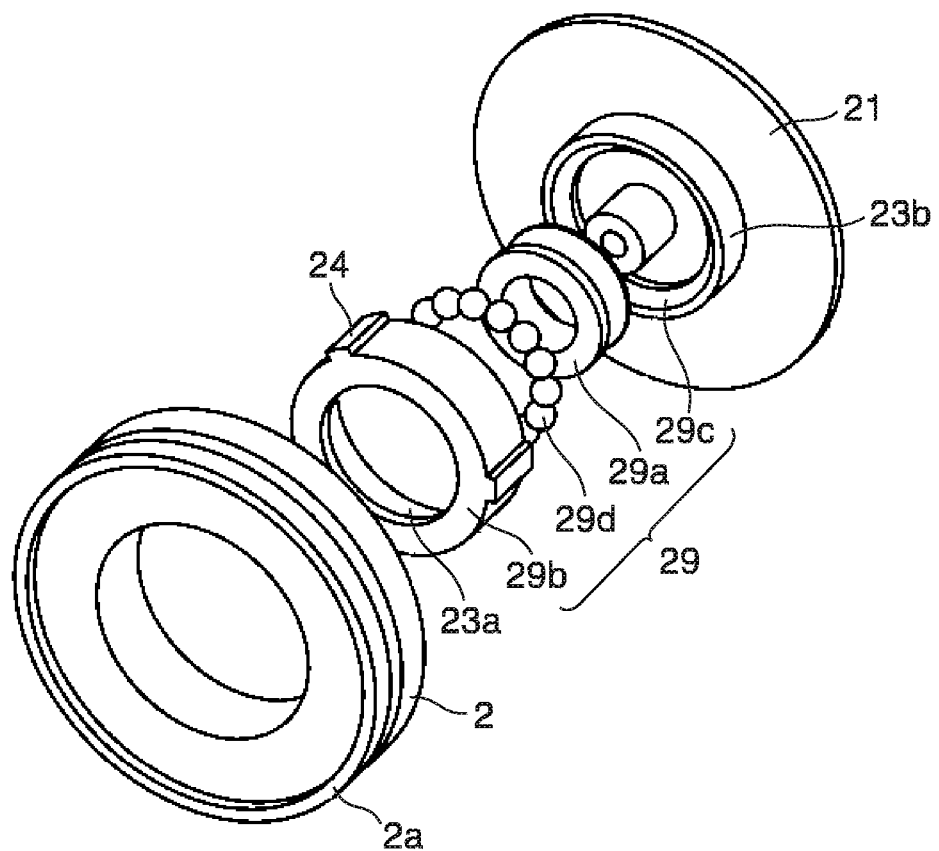
FIG. 12B is an exploded perspective view of the driven element, the bearing, and the flange shown in FIG. 12A.

FIG. 12A is a cross-sectional view of an assembled state of a driven element 2, a bearing 29, and a flange 21 as components of a vibration drive device according to the ninth embodiment of the present invention. FIG. 12B is an exploded perspective view of the driven element 2, the bearing 29, and the flange 21 shown in FIG. 12A. Note that illustration of components common to those of the vibration drive device 100 according to the first embodiment is omitted, and description thereof is also omitted.

The driven element 2 and the flange 21 are the same as described in the seventh embodiment. The extended portion 29b-e of the second bearing portion 29b has the outer peripheral surface thereof formed with a plurality of protruding portions 24 extending in the thrust direction. In the illustrated example, the protruding portions 24 are provided at three locations at circumferentially equally-spaced intervals.

To assemble the driven element 2, the bearing 29, and the flange 21 to each other, first, the first bearing portion 29a is disposed in the third bearing portion 29c. Then, a predetermined number of the rolling elements 29d are disposed in a raceway, and the second bearing portion 29b is threadedly engaged with the third bearing portion 29c while adjusting a fastening torque. With this, similar to the seventh embodiment, a force with which the second bearing portion 29b and the third bearing portion 29c are pressed against each other in the thrust direction is controlled to a predetermined value. Subsequently, the driven element 2 is fitted on the second bearing portion 29b along the protruding portions 24 formed on the outer peripheral surface of the second bearing portion 29b, and is brought into contact with the flange 21. The contact surfaces of the flange 21 and the driven element 2 are fixed to each other e.g. by an adhesive. Further, at least one of contact surfaces where the protruding portions 24 formed on the second bearing portion 29b and the inner peripheral surface of the driven element 2 are brought into contact with each other is joined by an adhesive.

With this, similar to the seventh embodiment, the stiffness of the bearing 29 is prevented from being degraded by occurrence of loosening of threadedly engaged portions of the second and third bearing portions 29b and 29c. Further, since joined portions of the driven element 2 with the second bearing portion 29b are discretely provided, the driven element 2 is difficult to be influenced by a degree of roundness of the second bearing portion 29b or deformation of the second bearing portion 29b due to the movement of the rolling elements 29d, whereby it is possible to maintain excellent smoothness and flatness of the frictional sliding portion 2a.

Note that it is only required that the protruding portions 24 are formed at two or more locations on the second bearing portion 29b, and further they may be formed not on the second bearing portion 29b but on the driven element 2. Furthermore, after changing the shapes of the second bearing portion 29b and the third bearing portion 29c such that the outer peripheral surface of the third bearing portion 29c is brought into contact with the inner peripheral surface of the driven element 2, the protruding portions 24 may be formed on the outer peripheral surface of the third bearing portion 29c. The shapes of the second and third bearing portions 29b and 29c may be changed, for example, to provide an arrangement in which a portion corresponding to the extended portion 29b-e of the second bearing portion 29b is formed on the third bearing portion 29c, and the outer peripheral surface of the second bearing portion 29b is threadedly engaged with or fitted in an inner peripheral of the third bearing portion 29c.

The shape of the protruding portions 24 is not limited to a bar-like shape, but they may have a round shape, a spherical shape, a knurled shape, or the like. A gap between the driven element 2 and the second bearing portion 29b may be filled with an adhesive. This makes it possible to reinforce a force joining between the driven element 2 and the second bearing portion 29b.

Figure 13A:
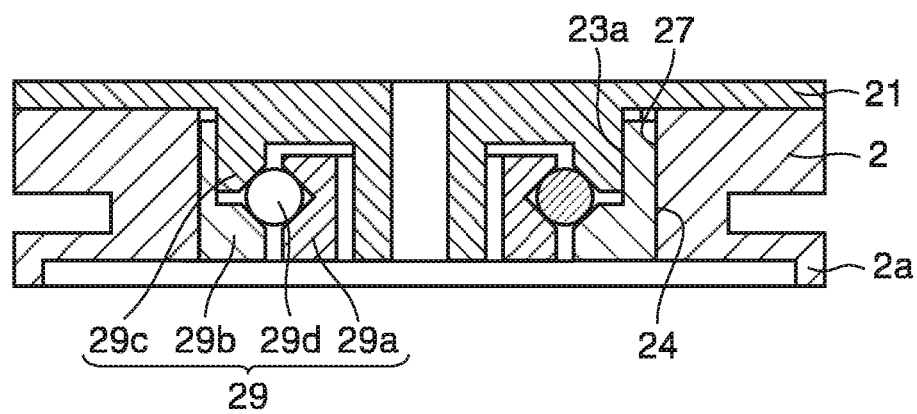
FIG. 13A is a cross-sectional view of an assembled state of a driven element, a bearing, and a flange as components of a vibration drive device according to a tenth embodiment of the present invention.
Figure 13B:
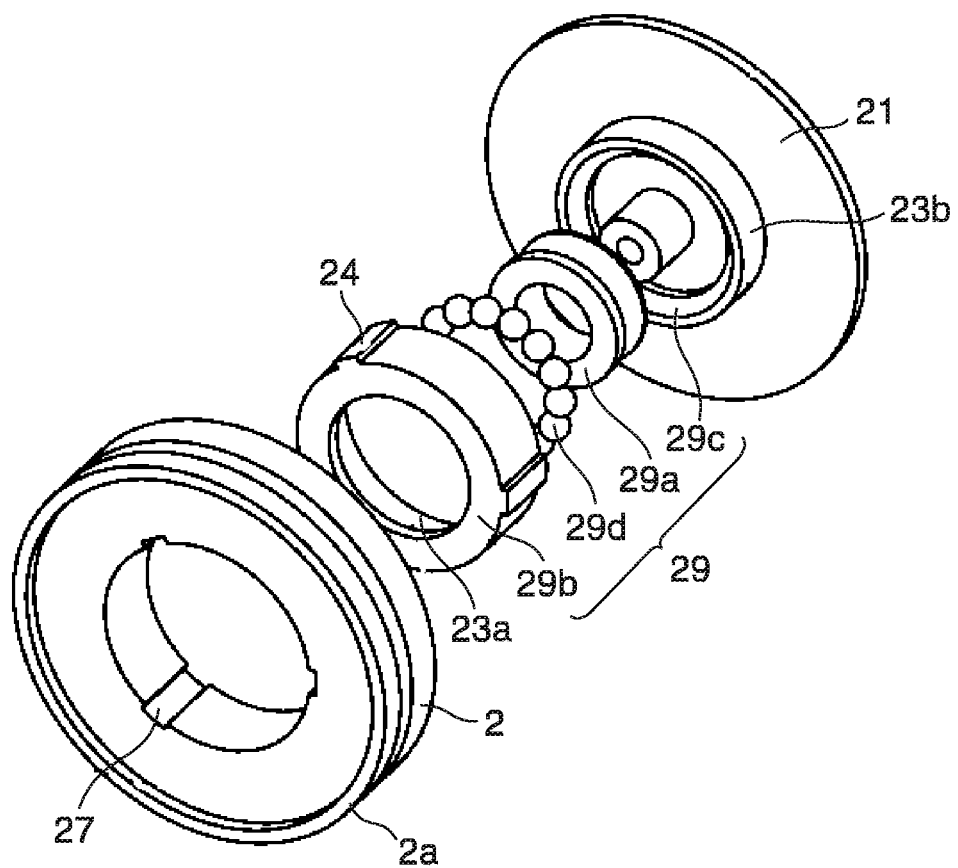
FIG. 13B is an exploded perspective view of the driven element, the bearing, and the flange shown in FIG. 13A.

FIG. 13A is a cross-sectional view of an assembled state of a driven element 2, a bearing 29, and a flange 21 as components of a vibration drive device according to a tenth embodiment of the present invention. FIG. 13B is an exploded perspective view of the driven element 2, the bearing 29, and the flange 21 shown in FIG. 13A. Note that illustration of components common to those of the vibration drive device 100 according to the first embodiment is omitted, and description thereof is also omitted.

The flange 21 is the same as described in the seventh embodiment. The second bearing portion 29b is the same as described in the ninth embodiment. The driven element 2 differs from the driven element 2 described in the ninth embodiment in that it has an inner peripheral surface formed with recessed portions 27 which are fitted in the protruding portions 24 formed on the second bearing portion 29b. By fitting the protruding portions 24 formed on the second bearing portion 29b in the recessed portions 27 formed in the driven element 2, it is possible to positively prevent the flange 21 and the driven element 2a from rotationally moving relative to each other, without causing a slip in the circumferential direction. Further, naturally, it is possible to obtain the same advantageous effects as provided by the ninth embodiment. The shapes for realizing the fitting between the second bearing portion 29b and the driven element 2 are not limited to the protruding shape and the recessed shape, but they may be a combination of one key and one key groove, consecutive protrusions and depressions, or gear shapes.

Figure 14A:
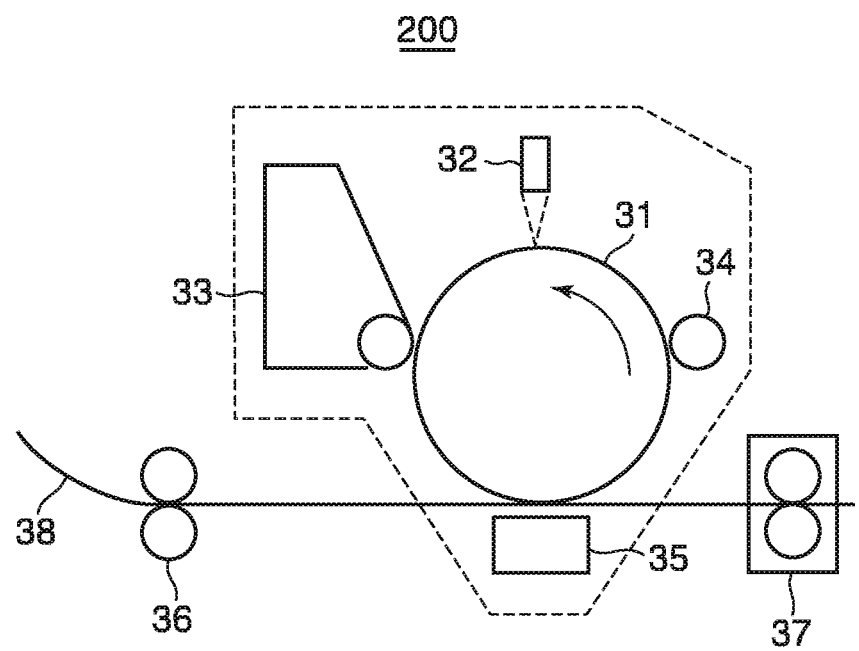
FIG. 14A is a partial schematic side view of an image forming apparatus using the vibration drive device shown in FIGS. 1A and 1B.

In an eleventh embodiment of the present invention, a description will be given of an image forming apparatus using the vibration drive device 100. FIG. 14A is a partial schematic side view of the image forming apparatus 200 using the vibration drive device 100.

The image forming apparatus 200 is e.g. a printer or a copy machine, and includes a photosensitive member 31, an exposure light source 32, a developing device 33, an electrostatic charger 34, a transfer device 35, and a conveying unit 36, and a fixing device 37. The electrostatic charger 34 charges the photosensitive member 31. Light is emitted from the exposure light source 32 toward a surface of the photosensitive member 31, and an electrostatic latent image is formed on the surface of the photosensitive member 31. The developing device 33 includes e.g. toner, and develops the electrostatic latent image with the toner. The transfer device 35 transfers a toner image formed on the photosensitive member 31 onto a recording medium 38, such as a sheet. The conveying unit 36 conveys the recording medium 38. The fixing device 37 fixes the toner image formed on the recording medium 38.

Figure 14B:
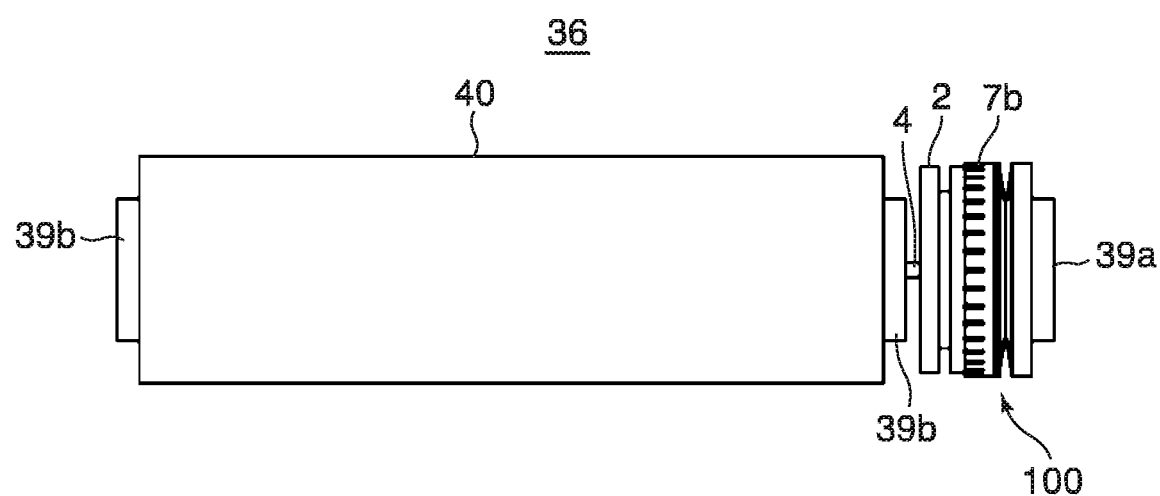
FIG. 14B is a schematic top view of a conveying unit provided in the image forming apparatus.

FIG. 14B is a schematic top view of the conveying unit 36. The conveying unit 36 includes a motor holding member 39a, a roller holding member 39b, the vibration drive device 100, and a roller 40.

The conveying unit 36 is held by the motor holding member 39a and the roller holding member 39b in a body (not shown) of the image forming apparatus 200. The vibration drive device 100 is capable of generating a high torque by frictionally driving the driven element 2. By making use of this characteristic, the output shaft 4 of the vibration drive device 100, which is directly connected to the roller 40, directly drives the roller 40. This makes it unnecessary to decelerate a motor by gears as in a case where an electromagnetic motor is used, so that it is possible to reduce e.g. variation in stop position accuracy due to the backlash of the gear, or gear driving noise, whereby it is possible to realize a conveying device with high accuracy and quietness. Further, since the vibration element 1 and the driven element 2 are in frictional contact with each other, it is possible to increase the start-up speed of the vibration drive device 100. Therefore, the conveying unit 36 is appropriate e.g. for an inkjet printer in which the movement and stop of a sheet are frequently repeated during printing. Note that the vibration drive device 100 is not limited to the use in the conveying unit 36, but it can also be used as a rotation drive device for the photosensitive member 31.

In a twelfth embodiment of the present invention, a description will be given of a positioning stage using the vibration drive device 100. As the positioning stage, there is a demand for one which performs fine machining or soldering with high accuracy, against the backdrop of downsizing and an increase in density of integrated circuits, and downsizing of electronic equipment. As for an arrangement in which a drive source for driving the stage is moved together with the stage, an increase in the size and weight of the whole positioning stage including the drive source causes variation in the stop position accuracy of the stage due to inertia, and hence there is a demand for reducing the size and weight of the whole positioning stage. In the positioning stage using a general electromagnetic motor, the motor is decelerated by a plurality of gears using a ball gear (planetary ball drive mechanism) to thereby improve positioning accuracy. In this case, however, the construction of the positioning stage becomes complicated, which makes it difficult to reduce the size and weight of the positioning stage.

Figure 15:
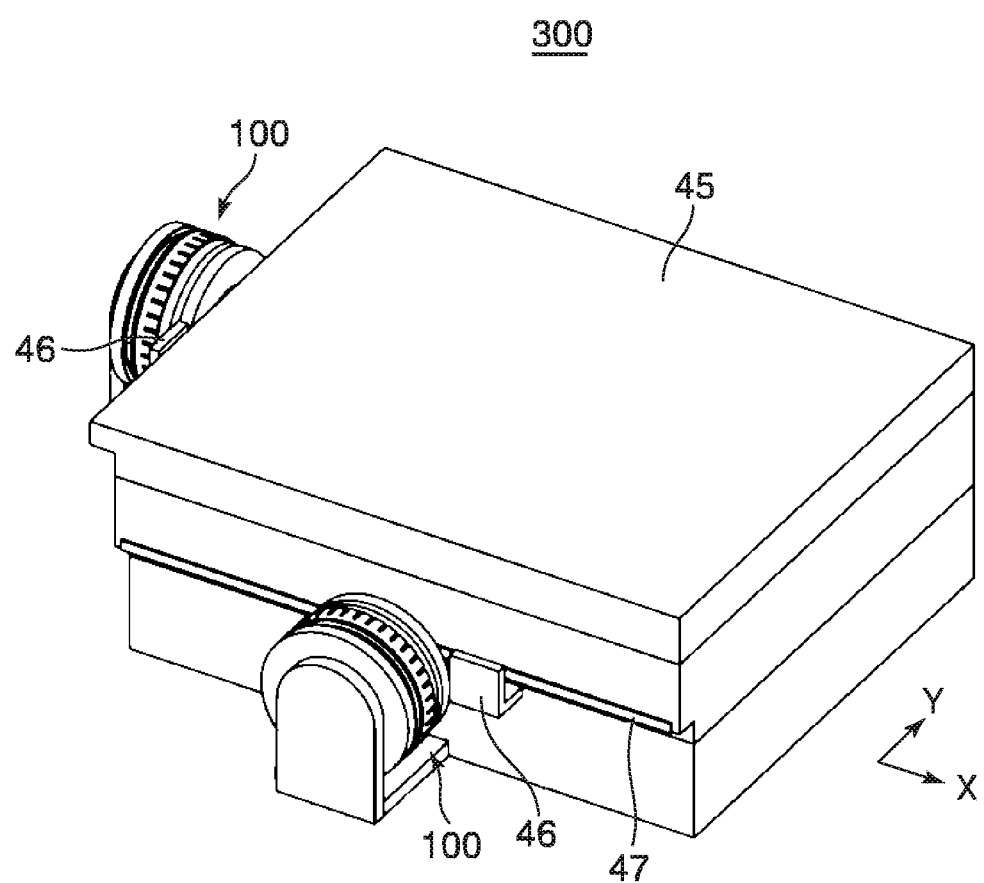
FIG. 15 is a schematic perspective view of a positioning stage using the vibration drive device shown in FIGS. 1A and 1B.

In contrast, by using the vibration drive device 100 as a drive source, it is possible to realize the positioning stage with high positioning accuracy by a simple construction, and also reduce the size and weight of the stage. FIG. 15 is a schematic perspective view of the positioning stage 300 using the vibration drive device 100. The positioning stage 300 is comprised of a stage 45, encoder sensors 46, and encoder scales 47. The stage 45 is driven by two vibration drive devices 100 for driving the stage in an X direction and a Y direction.

In the positioning stage 300 on which are installed the vibration drive devices 100 capable of performing a very small feed by friction driving, it is possible to perform low-speed driving by combining rack gears (not shown) arranged on the stage 45 and pinion gears (not shown) mounted on the vibration drive devices 100, respectively. By thus simplifying the construction of the positioning stage 300, it is possible to realize the reduction of the size and weight of the positioning stage 300, and improve the stop position accuracy thereof. Further, each encoder scale 47 provided on a corresponding side surface of a movable member of the positioning stage 300 is read by the associated encoder sensor 46, to detect the amount of relative movement of the stage 45. By feeding back the detected amount of relative movement to the drive control of the associated vibration drive device 100, it is possible to position the stage 45 with high accuracy.

Figure 16A:
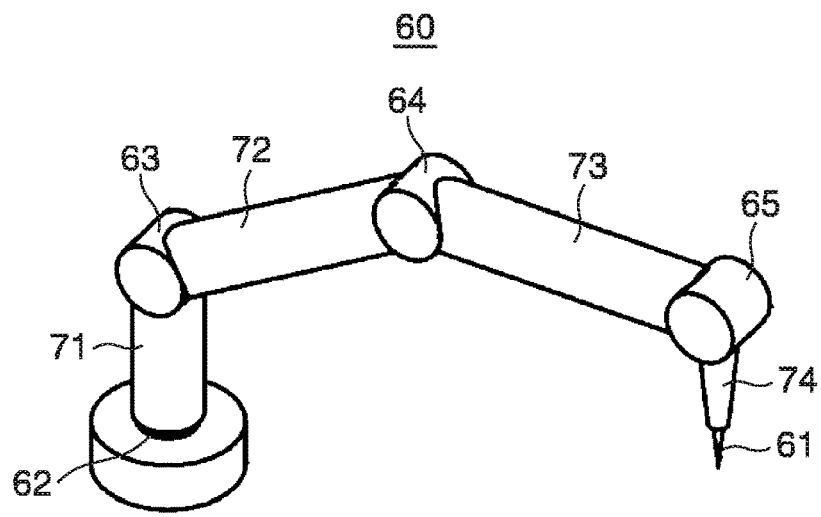
FIG. 16A is a schematic perspective view of a multi-joint robot using the vibration drive devices shown in FIGS. 1A and 1B.
Figure 16B:
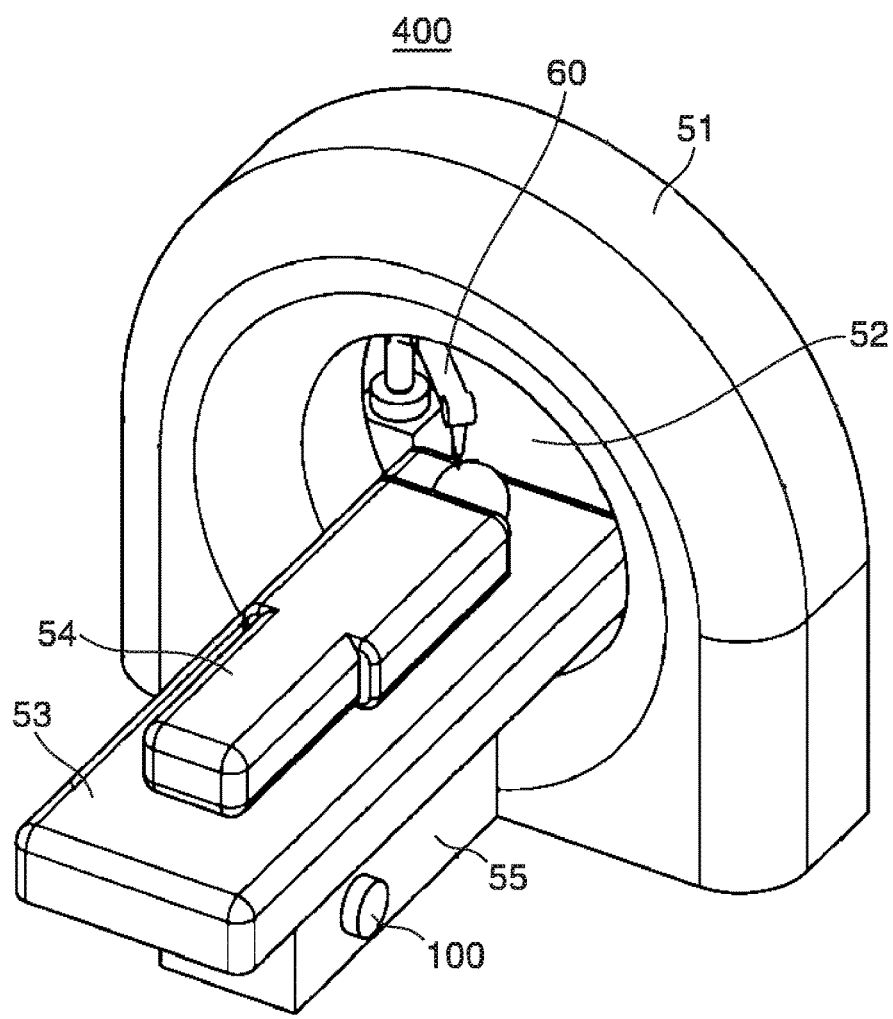
FIG. 16B is a schematic perspective view of an MRI diagnostic apparatus equipped with the multi-joint robot shown in FIG. 16A.

In a thirteenth embodiment of the present invention, a multi-joint robot using the vibration drive device 100 will be described. Here, a description is given of an example in which the multi-joint robot is applied to an MRI (Magnetic Resonance Imaging) diagnostic apparatus which is a medical system. FIG. 16A is a schematic perspective view of the multi-joint robot 60 using the vibration drive devices 100. FIG. 16B is a schematic perspective view of the MRI diagnostic apparatus 400 equipped with the multi-joint robot 60.

In the MRI diagnostic apparatus 400, a high magnetic field is generated, and therefore when a device using a material having magnetic properties, such as an electromagnetic motor that uses a magnet, is set for the MRI diagnostic apparatus 400, it is required to provide preventive measures for preventing a diagnostic image from being influenced by the magnetism of the material. In contrast, each vibration drive device 100 does not use a magnet, and hence can be installed in the vicinity of or within the MRI diagnostic apparatus 400.

The multi-joint robot 60 includes a medical instrument 61, and a multi-joint arm that holds the medical instrument 61 and is configured to be movable. The multi-joint arm has a four-axis vertical multi-joint structure in which a first arm 71, a second arm 72, a third arm 73, and a fourth arm 74 are coupled to each other in series via a first joint portion 62, a second joint portion 63, a third joint portion 64, and a fourth joint portion 65 each of which has one rotational degree of freedom. The vibration drive device 100 (not shown) is incorporated in each joint portion, and each vibration drive device 100 drives an associated one of the arms by causing an associated joint to perform a rotational motion. Then, the medical instrument 61 mounted on an end of the fourth arm 74 performs a desired medical procedure while acquiring image information of a subject 54 by the MRI diagnostic apparatus 400.

More specifically, as shown in FIG. 16B, the multi-joint robot 60 is arranged in the vicinity of the MRI diagnostic apparatus 400 which has an annular shape. The MRI diagnostic apparatus 400 is comprised of a magnetic field-generating section 51 having an annular shape, a bore 52 which is a hollow cylindrical portion into which the subject 54 is moved, a treatment table 53 on which the subject 54 is caused to lie, and a support base 55 which moves the treatment table 53 closer into or away from the bore 52. The multi-joint robot 60 is arranged at a location where the medical instrument 61 can be inserted into the bore 52.

The multi-joint robot 60 is driven based on the image information acquired by the MRI diagnostic apparatus 400, and medical treatment is performed by the medical instrument 61. Examples of the medical treatment include various types of operations and diagnoses, and examples of the medical instrument 61 include an end effector, a surgical knife, a forceps, a needle, a probe, and a diagnostic instrument.

The support base 55 as well is equipped with the vibration drive device 100 as a drive source for moving the treatment table 53. As described hereinabove, the vibration drive device 100 does not use a magnet, and therefore can be disposed close to the magnetic field-generating section 51. This makes it possible to increase the degree of freedom in designing the treatment table 53. Further, the vibration drive device 100 can be directly disposed in each joint portion of the multi-joint robot 60 to directly drive an associated one of the arms, whereby it is possible to reduce the number of component parts, such as gears and belts, for transmitting a driving force, and improve the responsiveness of medical equipment. Furthermore, since the entire multi-joint robot 60 can be made of a non-magnetic material, it is possible to minimize the influence of magnetism on image information of the subject 54 when medical treatment is performed within the bore 52.

Although in the present embodiment, the description is given of a case where the medical instrument 61 is inserted into the bore 52 of the annular-shaped MRI diagnostic apparatus 400, by way of example, the construction of the MRI diagnostic apparatus 400 is not limited to the annular shape. Further, although the four-axis vertical multi-joint structure has been described as the structure of the multi-joint robot 60, this is not limitative, but the multi-joint robot 60 may be a horizontal multi-joint type or a parallel link mechanism type. Furthermore, the degree of freedom in the operation of each joint portion, and the installation locations and the number of the vibration drive devices 100 are by no means limited to the above examples.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-093997 filed May 1, 2015 which is hereby incorporated by reference herein in its entirety.

What is claimed is:

1. A vibration drive device in which a vibration element and a driven element are brought into pressure contact with each other, and vibration is excited in the vibration element to thereby rotationally move the driven element relative to the vibration element,
    the vibration drive device including a bearing rotatably supporting the driven element,
    said bearing comprising:
    a plurality of rolling elements;
    a first bearing portion that has a first raceway surface in contact with said plurality of the rolling elements;
    a second bearing portion that has a second raceway surface in contact with said plurality of the rolling elements; and
    a third bearing portion that has a third raceway surface in contact with said plurality of the rolling elements,
    wherein said second bearing portion and said third bearing portion are joined to the driven element, and said second bearing portion and said third bearing portion are pressed against each other via said plurality of the rolling elements in a direction along an axis of said bearing, whereby said plurality of the rolling elements are brought into pressure contact with the first raceway surface, the second raceway surface, and the third raceway surface, and
    wherein one of said second bearing portion and said third bearing portion is integrally formed with the driven element from a same material.

2. The vibration drive device according to claim 1, further comprising a unit causing said second bearing portion and said third bearing portion to be pressed against each other via said plurality of the rolling elements in the direction along the axis of said bearing.

3. The vibration drive device according to claim 1, wherein one of said second bearing portion and said third bearing portion has a contact portion brought into contact with the driven element, and at least part of said contact portion is joined to the driven element.

4. The vibration drive device according to claim 3, wherein said contact portion includes a plurality portions discretely provided.

5. The vibration drive device according to claim 1, further comprising an output shaft that outputs a rotational driving force of the driven element to an outside, and
    a driving force transmission member that connects the driven element and said output shaft, and
    wherein said third bearing portion is integrally formed with said driving force transmission member from a same material.

6. The vibration drive device according to claim 5, wherein said driving force transmission member and the driven element are integrally formed with each other from the same material.

7. The vibration drive device according to claim 5, wherein said driving force transmission member is coupled to the driven element by a frictional force via a rubber member.

8. The vibration drive device according to claim 1, wherein the driven element is formed by a first component and a second component fastened to each other in the direction along the axis of said bearing,
    wherein said second bearing portion is integrally formed with said second component from a same material, and said third bearing portion is integrally formed with said first component from a same material, and
    wherein said second bearing portion and said third bearing portion are coupled to each other in a state pressed against each other via said plurality of the rolling elements in the direction along the axis of said bearing.

9. The vibration drive device according to claim 1, further comprising an urging unit configured to pressurize the vibration element against the driven element, and
    a base for supporting said urging unit, and
    wherein said first bearing portion is joined to said base.

10. A medical system including a multi-joint robot that performs a predetermined diagnosis or operation on a subject,
    wherein the multi-joint robot has a plurality of joint portions, and
    each of the joint portions incorporates a vibration drive device in which a vibration element and a driven element are brought into pressure contact with each other, and vibration is excited in the vibration element to thereby rotationally move the driven element relative to the vibration element, in order to enable each joint portion to perform rotational movement,
    the vibration drive device including a bearing rotatably supporting the driven element,
    the bearing comprising:
    a plurality of rolling elements;
    a first bearing portion that has a first raceway surface in contact with said plurality of the rolling elements;
    a second bearing portion that has a second raceway surface in contact with said plurality of the rolling elements; and
    a third bearing portion that has a third raceway surface in contact with said plurality of the rolling elements,
    wherein said second bearing portion and said third bearing portion are joined to the driven element, and said second bearing portion and said third bearing portion are pressed against each other via said plurality of the rolling elements in a direction along an axis of said bearing, whereby said plurality of the rolling elements are brought into pressure contact with the first raceway surface, the second raceway surface, and the third raceway surface, and
    wherein one of said second bearing portion and said third bearing portion is integrally formed with the driven element from a same material.

11. The medical system according to claim 10, further comprising a magnetic field-generating unit configured to generate a magnetic field, and
    wherein the multi-joint robot is arranged within or close to the magnetic field generated by said magnetic field-generating unit.

12. An image forming apparatus including:
    an image forming unit configured to form an image on a sheet using toner or ink, and a conveying unit configured to convey a sheet to said image forming unit or convey a sheet having a predetermined image formed thereon by the image forming unit, wherein the conveying unit is equipped with a vibration drive device which is connected to a roller driven for rotation for conveying a sheet and in which a vibration element and a driven element are brought into pressure contact with each other, and vibration is excited in the vibration element to thereby rotationally move the driven element relative to the vibration element, the vibration drive device including a bearing rotatably supporting the driven element, the bearing comprising:

a plurality of rolling elements;

a first bearing portion that has a first raceway surface in contact with said plurality of the rolling elements;

a second bearing portion that has a second raceway surface in contact with said plurality of the rolling elements; and a third bearing portion that has a third raceway surface in contact with said plurality of the rolling elements, wherein said second bearing portion and said third bearing portion are joined to the driven element, and are pressed against each other via said plurality of the rolling elements in a direction along an axis of said bearing, whereby said plurality of the rolling elements are brought into pressure contact with the first raceway surface, the second raceway surface, and the third raceway surface, and wherein one of said second bearing portion and said third bearing portion is integrally formed with the driven element from a same material.

13. A positioning stage including:

a vibration drive device in which a vibration element and a driven element are brought into pressure contact with each other, and vibration is excited in the vibration element to thereby rotationally move the driven element relative to the vibration element, and a stage that is moved in a predetermined direction by the vibration drive device, the vibration drive device including a bearing rotatably supporting the driven element, the bearing comprising:

a plurality of rolling elements;

a first bearing portion that has a first raceway surface in contact with said plurality of the rolling elements;

a second bearing portion that has a second raceway surface in contact with said plurality of the rolling elements; and a third bearing portion that has a third raceway surface in contact with said plurality of the rolling elements, wherein said second bearing portion and said third bearing portion are joined to the driven element, and are pressed against each other via said plurality of the rolling elements in a direction along an axis of said bearing, whereby said plurality of the rolling elements are brought into pressure contact with the first raceway surface, the second raceway surface, and the third raceway surface, and wherein one of said second bearing portion and said third bearing portion is integrally formed with the driven element from a same material.

* * * * *